(12) United States Patent
Cruanes et al.

(10) Patent No.: US 8,771,733 B2
(45) Date of Patent: Jul. 8, 2014

(54) PHARMACEUTICAL COMPOSITION CONTAINING AN ANTI-NUCLEATING AGENT

(75) Inventors: Maria T. Cruanes, Lansdale, PA (US); Wei Xu, North Wales, PA (US); Laura M. Artino, Oakhurst, NJ (US); Honggang Zhu, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1643 days.

(21) Appl. No.: 11/792,190

(22) PCT Filed: Dec. 2, 2005

(86) PCT No.: PCT/US2005/043675
§ 371 (c)(1),
(2), (4) Date: May 31, 2007

(87) PCT Pub. No.: WO2006/060681
PCT Pub. Date: Jun. 8, 2006

(65) Prior Publication Data
US 2008/0118559 A1  May 22, 2008

Related U.S. Application Data

(60) Provisional application No. 60/632,859, filed on Dec. 3, 2004.

(51) Int. Cl.
*A61K 31/519* (2006.01)
*A61K 9/20* (2006.01)
*A61K 31/513* (2006.01)

(52) U.S. Cl.
USPC .................. 424/464; 514/269; 514/259.5

(58) Field of Classification Search
USPC ........................................................ 424/464
See application file for complete search history.

(56) References Cited

U.S. PATENT DOCUMENTS

| 4,540,566 | A * | 9/1985 | Davis et al. ............ 424/480 |
|---|---|---|---|
| 6,369,094 | B1 | 4/2002 | Bentley et al. |
| 7,169,780 | B2 | 1/2007 | Crescenzi et al. |
| 7,217,713 | B2 | 5/2007 | Crescenzi et al. |
| 7,232,819 | B2 | 6/2007 | Di Francesco et al. |
| 7,414,045 | B2 | 8/2008 | Crescenzi et al. |
| 7,435,734 | B2 | 10/2008 | Crescenzi et al. |
| 7,459,452 | B2 | 12/2008 | Di Francesco et al. |
| 7,754,731 | B2 | 7/2010 | Belyk et al. |
| 2005/0075356 | A1 | 4/2005 | Di Francesco et al. |
| 2006/0046985 | A1 | 3/2006 | Crescenzi et al. |
| 2006/0122205 | A1 | 6/2006 | Belyk et al. |
| 2007/0259894 | A1 | 11/2007 | Kassahun |
| 2007/0292504 | A1 | 12/2007 | Pourkavoos |
| 2008/0176869 | A1 | 7/2008 | Crescenzi et al. |
| 2008/0275004 | A1 | 11/2008 | Crescenzi et al. |

FOREIGN PATENT DOCUMENTS

| GB | WO 03/035077 A1 * | 5/2003 |
|---|---|---|
| WO | WO 03/035077 A1 | 5/2003 |
| WO | WO 03/086319 A2 | 10/2003 |
| WO | WO 2004/058756 A1 | 7/2004 |
| WO | WO 2006/060711 A2 | 6/2006 |
| WO | WO 2006/060731 A2 | 6/2006 |

OTHER PUBLICATIONS

Amendment filed Nov. 20, 2009 in U.S. Appl. No. 11/293,678.
Notice of Allowance dated Mar. 8, 2010 and Issue Fee Transmittal dated Jun. 4, 2010 for U.S. Appl. No. 11/293,678.
Office actions dated Nov. 5, 2009 and May 4, 2010 and Amendments dated Aug. 5, 2009 and Feb. 5, 2010 for U.S. Appl. No. 11/792,118.
Kumprakob, Usanee, et al., "Permeation Enhancement of Ketoprofen Using a Supersaturated System With Antinucleant Polymers", Biol. Pharm. Bulletin. 2005, pp. 1684-1688, vol. 28, No. 9.
Yeoh. Thean Y., "Use of Polymer Additives to Inhibit Phenytoin Nucleation and Crystal Growth From Supersaturated Aqueous Solution", Abstract of Ph.D. Thesis., Purdue University 1994.

* cited by examiner

*Primary Examiner* — Janet Epps-Smith
*Assistant Examiner* — Audrea Buckley
(74) *Attorney, Agent, or Firm* — Jeffrey P. Bergman; Sheldon O. Heber

(57) ABSTRACT

Pharmaceutical compositions suitable for oral administration in solid dosage forms are described. The compositions comprise an effective amount of a drug compound in the form of a salt, wherein the drug salt is characterized by conversion to a less soluble form of the drug compound under certain pH conditions, and an anti-nucleating agent.

25 Claims, 2 Drawing Sheets

__US 8,771,733 B2__

PHARMACEUTICAL COMPOSITION CONTAINING AN ANTI-NUCLEATING AGENT

This application is the National Stage of International Application No. PCT/US2005/043675, filed on Dec. 2, 2005, which claims the benefit of U.S. Provisional Application No. 60/632,859, filed Dec. 3, 2004, the disclosure of which is incorporated by reference herein in its entirety.

FIELD OF THE INVENTION

The present invention is directed to pharmaceutical compositions for oral administration which comprise the salt of a drug product and an anti-nucleating agent, wherein the drug salt tends to convert to a less soluble form (e.g., a neutral, non-salt form) under the pH conditions found in the stomach or the intestinal tract.

BACKGROUND OF THE INVENTION

Orally administered drugs with relatively poor aqueous solubility can exhibit poor absorption in the gastrointestinal tract. The solubility of such drugs can often be improved by administering the drugs in the form of salts. On the other hand, some drug salts have relatively high solubility under certain pH conditions but convert to less soluble forms when the pH changes. Basic salts, for example, can be comparatively soluble in neutral or basic aqueous media, but can convert to a less soluble form under acidic conditions. When such drug salts are administered orally, their solubility can be lost or significantly reduced in the acidic conditions typically encountered in the stomach, leading again to poor absorption of the drug into the systemic circulation. On the other hand, acid salts can be comparatively soluble in strongly acidic media (e.g., pH<4), but convert to a less soluble form in less acidic conditions (e.g., pH of about 5 or higher). Oral administration of these drug salts can accordingly result in sufficient solubility in the stomach, but inadequate solubility in the less acidic environment of the intestinal tract, leading to poor overall absorption.

In some cases the problem can be overcome by administering a larger quantity of the drug salt (e.g., by increasing the size and/or frequency of the dose), so that an effective amount of the drug can enter circulation and reach the targeted site(s) in the body. A drawback to this approach is that it is wasteful of drug. Another drawback is that increasing the dose frequency can lead to inadvertent or intentional patient non-compliance with the drug regimen. In some cases, the insolubility problem is so severe that oral administration is not a practical option. Accordingly, there exists a need for new means that provide for the efficient and effective oral administration of such drugs and drug salts.

SUMMARY OF THE INVENTION

The present invention is directed to pharmaceutical compositions for oral administration that include a drug compound salt that converts to a less soluble form of the drug under certain acidic conditions. More particularly, the present invention includes a pharmaceutical composition for oral administration as a solid dose, which comprises (i) an effective amount of a drug compound in the form of a salt, wherein the salt is characterized by conversion of the drug compound to a less soluble form at an gastrointestinal-relevant pH (alternatively referred to herein as a "GI-relevant pH") above or below its native pH, and (ii) an anti-nucleating agent.

A pharmaceutical composition for oral administration as a "solid dose" means a pharmaceutical composition which is orally administered in any convenient solid form including, but not limited to powders, granules, pills, powder-filled capsules, granule-filled capsules, and tablets.

The term "gastrointestinal-relevant pH" (or "GI-relevant pH") refers to a liquid-phase aqueous medium which has a pH that is less than about 8. The term "native pH" refers to the pH resulting from the dissolution of the drug in water in the absence of buffer. The GI-relevant pH can be an acidic pH, wherein the term "acidic pH" refers to a liquid-phase aqueous medium which has a pH that is less than 7. The GI-relevant pH, acidic pH, and native pH are of course measured at the same temperature, which is typically physiological temperature (e.g., 37° C. for humans).

Conversion of the drug to a less soluble form refers to any chemical or non-chemical change in the form of the drug brought about by introducing the starting drug form (here a drug salt) to an aqueous medium having a GI-relevant pH (e.g., an acidic pH) that differs from the drug's native pH. The conversion can be a pH driven change in the ionization state of the drug (e.g., conversion from an ionized, soluble form of the drug to a charge-neutral insoluble form), or it can be a physical change in the drug (e.g., a change in its hydration state) with or without an accompanying change in ionization.

Drug compound salts suitable for use in the present invention include, for example, those which have a native pH in the neutral or basic range and which convert to a less soluble form in a liquid-phase aqueous medium having a pH of less than about 5 (e.g., a pH in a range of from about 2 to about 5), such as the medium typically found in the human stomach. Oral administration of such a drug salt to a human subject can result in relatively poor absorption and thus low oral bioavailability as a result of the salt's conversion to a comparatively insoluble form (e.g., disproportionation of a metal phenoxide salt with formation of the free phenol) in the acidic conditions encountered in the stomach. Other drug salts suitable for use in the present invention include, for example, those salts which have a strongly acidic native pH and which convert to a less soluble form in a liquid-phase aqueous medium having a pH in a range of from about 6 to about 8. Such orally administered salts can convert to relatively insoluble, poorly absorbed forms in the weakly acidic (i.e., pH of 6 to less than 7) to neutral or weakly basic conditions (pH of 7 to about 8) encountered in the intestinal tract. The present invention solves these problems by formulating the salt with an anti-nucleating agent. Oral formulations of the present invention containing an anti-nucleating agent have exhibited improved solubility in in vitro dissolution tests and improved pharmacokinetics (PK) in animal studies compared to analogous formulations not containing the anti-nucleating agent. Oral formulations of the present invention have also exhibited suitable PK in humans. Without wishing to be bound by any particular theory, it is believed that the anti-nucleating agent can sufficiently inhibit and/or delay precipitation (or, stated another way, can provide prolonged supersaturation) of the drug compound under the acidic conditions of the stomach or the pH conditions of the intestine, so as to permit the drug to be more efficiently absorbed into circulation.

Various embodiments, aspects and features of the present invention are either further described in or will be apparent from the ensuing description, examples and appended claims.

DETAILED DESCRIPTION OF THE INVENTION

Figure 1:
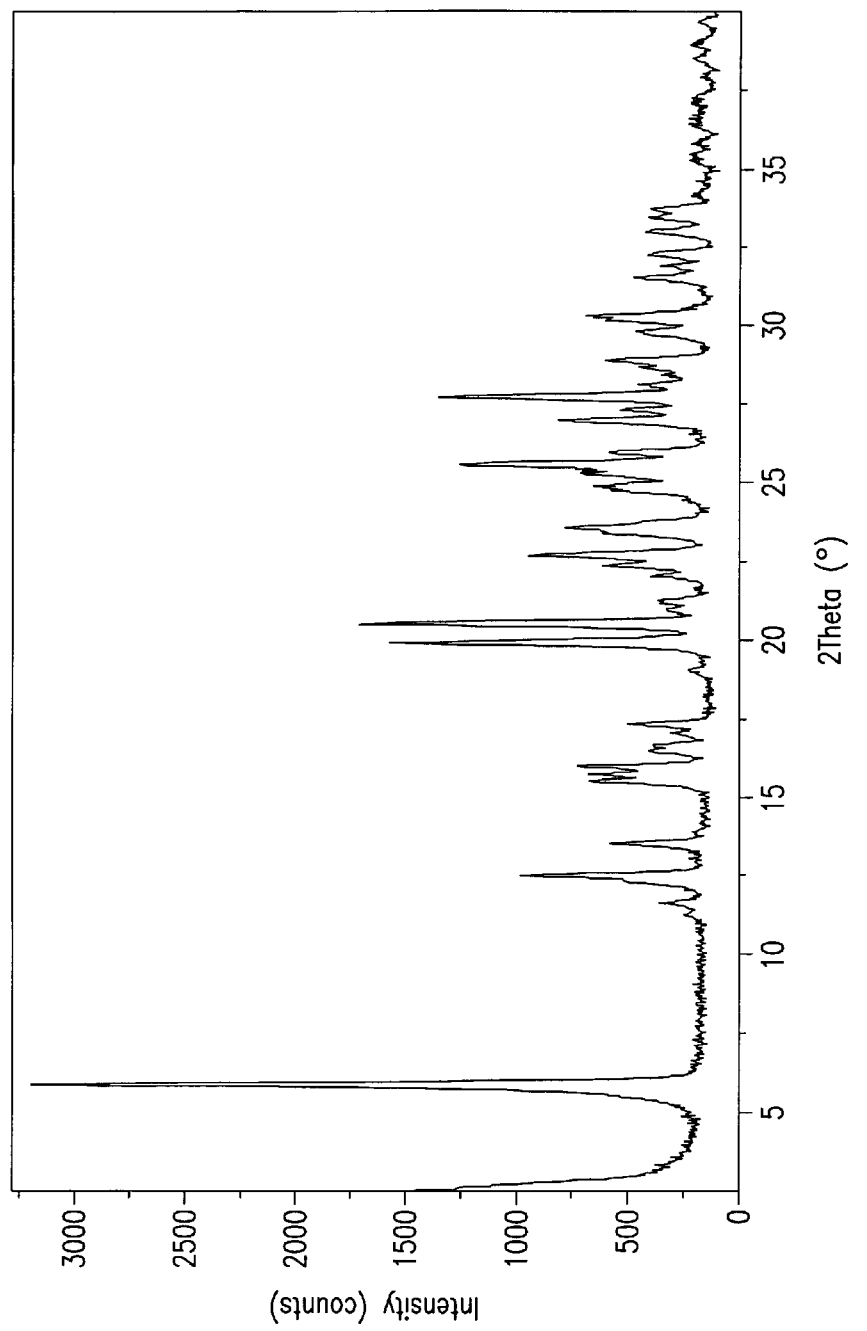
FIG. 1 is the X-ray powder diffraction pattern for the potassium salt of Compound A as prepared in Example 2.

Drug compound salts that can benefit from incorporation into a pharmaceutical composition of the present invention (i.e., those which convert to a less soluble form under certain pH conditions) can be identified by measuring the solubility of the drug as a function of pH so as to determine if there is a decrease in solubility under the pH conditions of interest relative to the solubility of the drug at its native pH. The following test may be used: The drug is added to a series of buffered aqueous solutions covering at suitable intervals a pH range that is above and below the pKa(s) of the drug, the native pH, and representative of physiological conditions. The drug may be added to each buffer solution with agitation over a period of time sufficient to achieve equilibrium conditions without compromising stability or, alternatively, for a time period relevant to residence times in the GI tract and, preferably, at 37° C. Drug is added until a point beyond which solid does not dissolve any further. The suspension is filtered and the concentration of the resulting clear solution is assayed (e.g., by spectroscopic and/or HPLC methods) to determine the actual concentration of drug in solution at each investigated pH. A solubility increase or decrease can be expected if there is a pH-driven ionization change in the molecule.

It is understood that the drug compound salts employed in pharmaceutical compositions embraced by the present invention are pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include base salts (also referred to herein as basic salts); i.e., salts formed by reaction of the drug compound with a base, including, for example, alkali metal salts (e.g., sodium or potassium salts), alkaline earth metal salts (e.g., calcium or magnesium salts) and ammonium salts. Alkali metal salts of the compounds can be formed by treating the compound dissolved in a suitable solvent with an aqueous solution of the alkali metal hydroxide (e.g., NaOH or KOH). Suitable salts also include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid.

As used herein, the term "composition" is intended to encompass a product comprising the specified ingredients, as well as any product which results, directly or indirectly, from combining the specified ingredients.

The term "effective amount" as used herein means that amount of active compound or pharmaceutical agent that elicits the biological or medicinal response in a tissue, system, animal or human that is being sought by a researcher, veterinarian, medical doctor or other clinician. The effective amount can be a "therapeutically effective amount" for the alleviation of the symptoms of the disease or condition being treated. The effective amount can also be a "prophylactically effective amount" for prophylaxis of the symptoms of the disease or condition being prevented. When the drug compound inhibits the action of an enzyme (e.g., HIV integrase—see below), the term also refers to the amount of active compound sufficient to inhibit the enzyme and thereby elicit the response being sought (i.e., an "inhibition effective amount").

Anti-nucleating agents suitable for use with a particular salt of a drug compound can be identified by performing solubility tests with the salt under the appropriate pH conditions (e.g., an aqueous medium buffered at a suitable pH and held at ambient—20 to 25° C.—or physiological—37° C.—temperature) in the presence and absence of a particular anti-nucleating agent, wherein exhibition of prolonged supersaturation of the compound in the presence of the anti-nucleating agent indicates the agent's suitability. The tests can be conducted with a single anti-nucleating agent at a series of concentrations to find a suitable concentration for further testing. The tests can also be conducted with a series of agents, each at the same concentration or series of concentrations, to select one or more agents for further screening via additional in vitro tests and/or in vivo PK studies.

A suitable solubility test for a drug salt characterized by a native pH in the neutral or basic pH range and by conversion to a less soluble form under highly acidic conditions is as follows: An unbuffered solution of the drug compound salt (5 to 10 mL) is introduced into a USP II dissolution vessel (i.e., a dissolution vessel equipped with a stirring paddle connected by a stirring shaft to a variable speed motor) containing a buffer solution (pH=2-4; 500 to 900 mL) equilibrated at 37° C. with or without an anti-nucleating agent, wherein the initial total drug concentration in the dissolution vessel is about 5× to 10× the equilibrium solubility of the neutral drug in the buffer. The solution is stirred (e.g., 50 rpm), and may become turbid due to precipitation of the neutral form of the drug. Samples are removed from the medium at periodic time intervals (e.g., 5, 10, 15, 20, 30, 60, 120, 180 and 240 minutes) and filtered (0.2 μm filter). The filtrate is diluted with a suitable solvent in which the solubility of the drug is higher than the initial total drug concentration in the media. The concentration of the drug in the diluted solution sample is then determined via HPLC analysis or UV spectrophotometry. Plots of drug solubility in the buffered solution in the presence and absence of an nucleating agent against time are then used to assess the efficacy of the agent in prolonging drug supersaturation. The use of this test is exemplified in Example 4 below. The same type of test, with suitable adjustment of the pH range, can be used to identify anti-nucleating agents suitable for use with drug salts characterized by a native pH in the strongly acidic pH range and by conversion to a less soluble form under weakly acidic or basic conditions.

An embodiment of the present invention is the pharmaceutical composition as originally defined above (i.e., the composition set forth in the Summary of the Invention), wherein the anti-nucleating agent comprises a water-soluble polymer. The term "water-soluble polymer" refers herein to any polymer which is freely soluble in water or which dissolves or solubilizes in water in an amount sufficient to provide anti-nucleating activity in compositions of the present invention (e.g., in an amount of at least about 0.005 mg/ml). Suitable water-soluble polymers include hydroxyalkylcelluloses, alkylcelluloses, polyvinylpyrrolidones, and polyacrylic acids. Suitable hydroxyalkylcelluloses include hydroxypropylmethylcellulose (HPMC), hydroxyethylcellulose, and hydroxypropylcellulose. A suitable alkylcellulose is methylcellulose. The water-soluble polymers can be employed in the present invention singly or in mixtures. It is known in the art to use the water-soluble polymers just described as stabilizing agents in pharmaceutical formulations; e.g., they can be employed to prevent or minimize settling of drug particles in dispersions before their administration (oral or otherwise) to patients. In the present invention, these polymers are employed as anti-nucleating agents; i.e., their primary role is to inhibit and/or delay precipitation of the drug in the subject's stomach and/or intestine after oral administration.

Another embodiment of the present invention is the pharmaceutical composition as originally set forth above, wherein the anti-nucleating agent comprises a low-viscosity, water-soluble polymer. The term "low viscosity" means that the water-soluble polymer produces a 2 wt. % (i.e., weight of polymer/weight of water) aqueous solution having a viscosity in a range of from about 2 to about 100 centipoise (cps) at 20° C. (1 cps=1 mPa sec). The low-viscosity, water-soluble polymer typically produces a 2 wt. % solution having a viscosity in a range of from about 2 to about 50 cps (e.g., from about 3 to about 20 cps) at 20° C. Suitable low-viscosity, water-soluble polymers include hydroxyalkylcelluloses, alkylcelluloses, polyvinylpyrrolidones, and polyacrylic acids. Suitable hydroxyalkylcelluloses include hydroxypropylmethylcellulose (HPMC), hydroxyethylcellulose, and hydroxypropylcellulose. A suitable alkylcellulose is methylcellulose. The low-viscosity, water-soluble polymers can be used singly or in mixtures of two or more (e.g., two or more HPMC polymers), wherein the polymer mixture produces a 2 wt. % solution with an average viscosity in the low viscosity range. The average viscosity of the polymer mixture typically differs from the viscosity of each component polymer.

Still another embodiment of the present invention is the pharmaceutical composition as originally set forth above, wherein the anti-nucleating agent comprises a hydroxyalkylcellulose. In an aspect of this embodiment, the anti-nucleating agent is HPMC (or a mixture of two or more HPMCs). Suitable HPMCs include those (whether singly or in mixtures) that produce 2 wt. % aqueous solutions of polymer in water with viscosities in a range of from about 3 to about 150,000 cps at 20° C. Suitable HPMCs include those sold under the trademark METHOCEL® (Dow Chemical) (e.g., METHOCEL grades K100LVP, K4M, K15M, and K100M) and METOLOSE® (Shin-Etsu). Suitable HPMCs also include U.S. Pharmacopeia standard substitution types 2208, 2906 and 2910.

Still another embodiment of the present invention is the pharmaceutical composition as originally set forth above, wherein the anti-nucleating agent comprises a low-viscosity hydroxyalkylcellulose. In an aspect of this embodiment, the anti-nucleating agent is HPMC (or a mixture of two or more HPMCs) that produces a 2 wt. % aqueous solution having a viscosity in a range of from about 2 to about 100 cps at 20° C. In another aspect of this embodiment, the anti-nucleating agent is an HPMC (or a mixture of two or more HPMCs) that produces a 2 wt. % aqueous solution having a viscosity in a range of from about 2 to about 50 cps (e.g., from about 3 to about 20 cps) at 20° C. In still another aspect, the anti-nucleating agent is an HPMC having a hydroxypropyl content of from about 7 to about 12 wt. %, a methoxy content of from about 28 to about 30 wt. %, and a viscosity for 2% w/w aqueous solutions of from about 3 to about 20 cps. In yet another aspect, the HPMC is U.S. Pharmacopeia standard substitution type 2208, 2906 or 2910, such as HPMC 2910 (6 cps) which is available as PHARMACOAT from Shin-Etsu Chemical Co.

Another embodiment of the present invention is the pharmaceutical composition as originally set forth above or as set forth in any one of the preceding embodiments, wherein the salt of the drug compound is employed in an amount of at least about 5 wt. % (e.g., at least about 10 wt. %) with respect to the total weight of the composition. Unless expressly stated to the contrary, any reference herein to the amount of the drug compound salt is to the amount of the free form of the compound. Thus, in this embodiment, the salt of the drug compound is employed in an amount which is equivalent to at least about 5 wt. % of the free (i.e., non-salt) form of the drug compound.

Another embodiment of the present invention is the pharmaceutical composition as originally set forth above or as set forth in any one of the preceding embodiments, wherein the anti-nucleating agent is employed in an amount of at least about 0.5 wt. % (e.g., at least about 1 wt. %) based on the total weight of the composition.

Another embodiment of the present invention is the pharmaceutical composition as originally set forth above or as set forth in any one of the preceding embodiments, wherein the salt of the drug compound is employed in an amount of from about 5 to about 75 wt. % and the anti-nucleating agent is employed in an amount of at least about 0.5 wt. % (e.g., at least about 1 wt. %), based on the total weight of the composition. Aspects of this embodiment include the pharmaceutical composition as just set forth, in which the following amounts of the drug compound salt and anti-nucleating agent (e.g., HPMC, such as a low-viscosity HPMC) are employed:

| Wt. % Drug Salt | Wt. % Anti-nucleating agent |
|---|---|
| from about 5 to about 75 | from about 0.5 to about 20 |
| from about 5 to about 75 | from about 1 to about 20 |
| from about 5 to about 75 | from about 2 to about 15 |
| from about 5 to about 60 | from about 0.5 to about 20 |
| from about 5 to about 60 | from about 1 to about 20 |
| from about 5 to about 60 | from about 2 to about 15 |
| from about 15 to about 50 | from about 0.5 to about 20 |
| from about 15 to about 50 | from about 1 to about 20 |
| from about 15 to about 50 | from about 2 to about 15 |

Another embodiment of the present invention is the pharmaceutical composition as originally set forth above or as set forth in any one of the preceding embodiments, which further comprises a diluent, a disintegrant and a lubricant.

Another embodiment of the present invention is the pharmaceutical composition as originally set forth above or as set forth in any one of the preceding embodiments, wherein the composition is encapsulated or compressed into a tablet.

Another embodiment of the present invention is a pharmaceutical composition for oral administration as a solid dose (alternatively referred to herein as "Composition C1" or the "C1 composition"), which comprises an effective amount of a base salt of a compound of Formula I (alternatively and more simply referred to herein as "Compound I") and an anti-nucleating agent, wherein Formula I is:

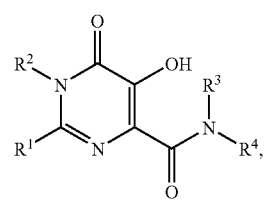

wherein $R^1$ is $C_{1-6}$ alkyl substituted with:
(1) $N(R^A)—C(=O)—N(R^C)R^D$,
(2) $N(R^A)—C(=O)—C_{1-6}$ alkylene-$N(R^C)R^D$,
(3) $N(R^A)SO_2R^B$,
(4) $N(R^A)SO_2N(R^C)R^D$,
(5) $N(R^A)—C(=O)—C_{1-6}$ alkylene-$SO_2R^B$,
(6) $N(R^A)—C(=O)—C_{1-6}$ alkylene-$SO_2N(R^C)R^D$,
(7) $N(R^A)C(=O)C(=O)N(R^C)R^D$, (8) N(R$^A$)—C(=O)—HetA,
(9) N(R$^A$)C(=O)C(=O)—HetA, or
(10) HetB;

R$^2$ is —C$_{1-6}$ alkyl;

or alternatively R$^1$ and R$^2$ are linked together such that the compound of Formula I is a compound of Formula II:

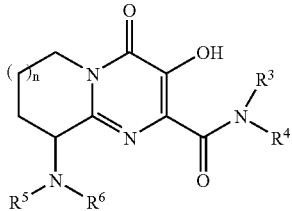

(II)

R$^3$ is —H or —C$_{1-6}$ alkyl;
R$^4$ is C$_{1-6}$ alkyl substituted with an aryl (e.g., phenyl), which is optionally substituted with from 1 to 4 substituents each of which is independently halogen, —OH, —C$_{1-4}$ alkyl, —C$_{1-4}$ alkyl-OR$^A$, —C$_{1-4}$ haloalkyl, —O—C$_{1-4}$ alkyl, —O—C$_{1-4}$ haloalkyl, —CN, —NO$_2$, —N(R$^A$)R$^B$, —C$_{1-4}$ alkyl-N(R$^A$)R$^B$, —C(=O)N(R$^A$)R$^B$, —C(=O)R$^A$, —CO$_2$R$^A$, —C$_{1-4}$ alkyl-CO$_2$R$^A$, —OCO$_2$R$^A$, —SR$^A$, —S(=O)R$^A$, —SO$_2$R$^A$, —N(R$^A$)SO$_2$R$^B$, —SO$_2$N(R$^A$)R$^B$, —N(R$^A$)C(=O)R$^B$, —N(R$^A$)CO$_2$R$^B$, —C$_{1-4}$ alkyl-N(R$^A$)CO$_2$R$^B$, methylenedioxy attached to two adjacent ring carbon atoms, phenyl, or —C$_{1-4}$ alkyl-phenyl;
R$^5$ is:
(1) N(R$^A$)—C(=O)—N(R$^C$)R$^D$,
(2) N(R$^A$)—C(=O)—C$_{1-6}$ alkylene-N(R$^C$)R$^D$,
(3) N(R$^A$)SO$_2$R$^B$,
(4) N(R$^A$)SO$_2$N(R$^C$)R$^D$,
(5) N(R$^A$)—C(=O)—C$_{1-6}$ alkylene-SO$_2$R$^B$,
(6) N(R$^A$)—C(=O)—C$_{1-6}$ alkylene-SO$_2$N(R$^C$)R$^D$,
(7) N(R$^A$)C(=O)C(=O)N(R$^C$)R$^D$,
(8) N(R$^A$)—C(=O)—HetA, or
(9) N(R$^A$)C(=O)C(=O)—HetA;
R$^6$ is —H or —C$_{1-6}$ alkyl;
n is an integer equal to 1 or 2;
each R$^A$ is independently —H or —C$_{1-6}$ alkyl;
each R$^B$ is independently —H or —C$_{1-6}$ alkyl;
R$^C$ and R$^D$ are each independently —H or —C$_{1-6}$ alkyl, or together with the nitrogen to which they are attached form a saturated 5- or 6-membered heterocyclic ring optionally containing a heteroatom in addition to the nitrogen attached to R$^C$ and R$^D$ selected from N, O, and S, where the S is optionally oxidized to S(O) or S(O)$_2$, and wherein the saturated heterocyclic ring is optionally substituted with 1 or 2 C$_{1-6}$ alkyl groups;
HetA is a 5- or 6-membered heteroaromatic ring containing from 1 to 4 heteroatoms independently selected from N, O and S, wherein the heteroaromatic ring is optionally substituted with 1 or 2 substituents each of which is independently —C$_{1-4}$ alkyl, —C$_{1-4}$ haloalkyl, —O—C$_{1-4}$ alkyl, —O—C$_{1-4}$ haloalkyl, or —CO$_2$R$^A$; and
HetB is a 5- to 7-membered saturated heterocyclic ring containing from 1 to 4 heteroatoms independently selected from N, O and S, wherein each S is optionally oxidized to S(O) or S(O)$_2$, and the heterocyclic ring is optionally substituted with from 1 to 3 substituents each of which is independently halogen, —C$_{1-4}$ alkyl, —C$_{1-4}$ fluoroalkyl, —C(O)—C$_{1-4}$ alkyl, or —C$_{1-4}$ alkyl substituted with OH.

In an aspect of the preceding embodiment, in the compound of Formula I, R$^2$ is methyl; R$^3$ is —H; and R$^4$ is CH$_2$-phenyl wherein the phenyl is optionally substituted with 1 or 2 substituents each of which is independently bromo, chloro, fluoro, CH$_3$, CF$_3$, C(O)NH$_2$, C(O)NH(CH$_3$), C(O)N(CH$_3$)$_2$, SCH$_3$, SO$_2$CH$_3$, or SO$_2$N(CH$_3$)$_2$; and all other variables are as defined above. In a feature of this aspect, R$^4$ is 4-fluorobenzyl, 3,4-dichlorobenzyl, 3-chloro-4-fluorobenzyl, or 4-fluoro-3-methylbenzyl. In another feature of this aspect, R$^4$ is 4-fluorobenzyl.

The compounds of Formula I are HIV integrase inhibitors. More particularly, representative compounds embraced by Formula I have been tested in an integrase inhibition assay in which strand transfer is catalyzed by recombinant integrase, and have been found to be active inhibitors of HIV integrase. Integrase inhibition activity can be determined, for example, using the assay described in Hazuda et al., *J. Virol.* 1997, 71: 7005-7011. Representative compounds have also been found to be active in an assay for the inhibition of acute HIV infection of T-lymphoid cells conducted in accordance with Vacca et al., *Proc. Natl. Acad. Sci. USA* 1994, 91: 4096-4100. Further description of representative compound embraced by Formula I, methods for their preparation, and assays for measuring their integrase inhibition activity and their inhibition of HIV replication can be found in WO 03/035077, the disclosure of which is herein incorporated by reference in its entirety. The base salts (e.g., the alkali metal salts) of these compounds are typically soluble in neutral or basic aqueous media (i.e., they typically have a native pH≥7), but convert via disproportionation to a less soluble, free phenol form under acidic conditions, as a result of which the compounds can exhibit poor absorption and low bioavailability when administered orally. Formulating the Compound I base salts with anti-nucleating agents can result in improved oral bioavailability.

Another embodiment of the present invention is Composition C1 as set forth above, wherein the base salt of Compound I is an alkali metal salt of Compound I (e.g., a Na or K salt of Compound I).

Another embodiment of the present invention is Composition C1 as set forth above, wherein the base salt of Compound I is a base salt of Compound A (e.g., an alkali metal salt of Compound A such as the Na salt or the K salt), wherein Compound A is:

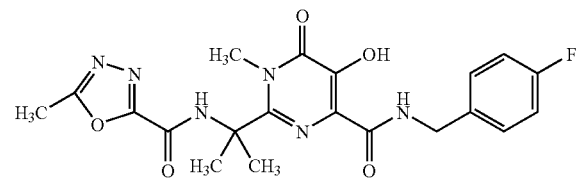 [SMILES: Cc1nnc(C(=O)NC(C)(C)c2nc(C(=O)NCc3ccc(F)cc3)c(O)c(=O)n2C)o1]

Still another embodiment of the present invention is Composition C1 as set forth above, wherein the base salt of Compound I is a potassium salt of Compound A. In an aspect of this embodiment, the potassium salt of Compound A is Form I crystalline potassium salt of Compound A, wherein the Form 1 K salt is an anhydrous crystalline salt characterized by an X-ray powder diffraction pattern obtained using copper K$_α$ radiation (i.e., the radiation source is a combination of Cu K$_{α1}$ and K$_{α2}$ radiation) which comprises 2Θ values (i.e., reflections at 2Θ values) in degrees of 5.9, 12.5, 20.0, 20.6 and 25.6.

Still other embodiments of the present invention include Composition C1 as originally set forth above and as set forth in any of the preceding embodiments of Composition C1, in which one or more of the following features (i) to (v) is (are) incorporated:

(i-a) the Compound I base salt is employed in an amount of at least about 5 wt. %;

(i-b) the Compound I base salt is employed in an amount of at least about 10 wt. %; or (i-c) the Compound I base salt is employed in an amount in a range of from about 5 to about 75 wt. %, or from about 5 to about 60 wt. %, or from about 15 to about 50 wt. %;

(ii-a) the anti-nucleating agent is employed in an amount of at least about 0.5 wt. %;

(ii-b) the anti-nucleating agent is employed in an amount of at least about 1 wt. %; or (ii-c) the anti-nucleating agent is employed in an amount in a range of from about 0.5 to about 20 wt. %, or from about 1 to about 20 wt. %, or from about 2 to about 15 wt. %;

(iii-a) the anti-nucleating agent comprises a water-soluble polymer selected from the group consisting of hydroxyalkylcellulose, alkylcellulose, polyvinylpyrrolidone and polyacrylic acid, and methylcellulose;

(iii-b) the anti-nucleating agent comprises a low-viscosity, water-soluble polymer selected from the group consisting of hydroxyalkylcellulose, alkylcellulose, polyvinylpyrrolidone and polyacrylic acid, and methylcellulose;

(iii-c) the anti-nucleating agent comprises a hydroxyalkylcellulose (e.g., a low-viscosity hydroxyalkylcellulose); or (iii-d) the anti-nucleating agent is HPMC (e.g. a low-viscosity HPMC such as HPMC 2910);

(iv-a) Composition C1 further comprises a diluent, a disintegrant, and a lubricant;

(iv-b) Composition C1 further comprises a diluent which is microcrystalline cellulose, a disintegrant which is croscarmellose sodium, and a lubricant which is magnesium stearate;

(iv-c) Composition C1 further comprises a first diluent, a second diluent, a disintegrant, and a lubricant;

(iv-d) Composition C1 further comprises a first diluent which is microcrystalline cellulose, a second diluent with is lactose or dibasic calcium phosphate, a disintegrant which is croscarmellose sodium, and a lubricant which is magnesium stearate; or (iv-e) Composition C1 further comprises from about 10 to about 85 wt. % of a first diluent (e.g., microcrystalline cellulose), from about 10 to about 85 wt. % of a second diluent (e.g., lactose or dibasic calcium phosphate), from about 1 to about 10 wt. % of a disintegrant (e.g., croscarmellose sodium), and from about 0.5 to about 10 wt. % of a lubricant (e.g., magnesium stearate); and (v-a) Composition C1 is encapsulated;

(v-b) Composition C1 is encapsulated to provide a capsule containing the Compound I base salt in an amount of from about 5 mg to about 1000 mg (e.g., from about 5 mg to about 900 mg, or from about 5 mg to about 600 mg, or from about 10 mg to about 400 mg);

(v-c) Composition C1 is compressed into a tablet; or (v-d) Composition C1 is compressed into a tablet containing the Compound I base salt in an amount of from about 5 mg to about 1000 mg (e.g., from about 5 mg to about 900 mg, or from about 5 mg to about 600 mg, or from about 10 mg to about 400 mg).

It is again noted that any reference herein to an amount the drug compound salt means the amount of the drug in its free, non-salt form. Thus, for example, a tablet composition containing Compound I base salt in an amount of from about 5 mg to about 1000 mg means a tablet composition containing an amount of the drug salt equivalent to about 5 mg to about 1000 mg of the Compound I parent (free phenol).

Still another embodiment of the present invention is a pharmaceutical composition for oral administration (alternatively referred to herein as "Composition C2" or the "C2 composition") as a solid dose, which comprises from about 5 to about 75 wt. % (e.g., from about 5 to about 60 wt. %) of a potassium salt of Compound A, from about 0.5 to about 20 wt. % (e.g., from about 2 to about 15 wt. %) HPMC (e.g., a low-viscosity HPMC such as HPMC 2910), from about 10 to about 85 wt. % (e.g., from about 15 to about 75 wt. %) microcrystalline cellulose, from about 10 to about 85 wt. % (e.g., from about 10 to about 50 wt. %) lactose or dibasic calcium phosphate, from about 1 to about 10 wt. % (e.g., from about 1 to about 5 wt. %) croscarmellose sodium, and from about 0.5 to about 10 wt. % (e.g., from about 0.5 to about 3 wt. %) magnesium stearate. In an aspect of this embodiment, the potassium salt of Compound A in Composition C2 is Form 1 potassium salt of Compound A. In another aspect, Composition C2 is encapsulated or compressed into a tablet. In a feature of this aspect, the capsule or tablet contains the potassium salt of Compound A (e.g., Form 1) in an amount of from about 5 mg to about 900 mg (e.g., from about 5 mg to about 600 mg, or from about 10 mg to about 400 mg).

Still another embodiment of the present invention is a pharmaceutical composition for oral administration (alternatively referred to herein as "Composition C3" or the "C3 composition") as a solid dose, which comprises about 50 wt. % of a potassium salt of Compound A and from about 0.5 to about 20 wt. % (e.g., from about 1 to about 20 wt. %, or from about 2 to about 15 wt. %, or about 5 wt. %) HPMC (e.g., a low-viscosity HPMC such as HPMC 2910). In an aspect of this embodiment, the composition further comprises from about 10 to about 85 wt. % (e.g., from about 15 to about 75 wt. %) microcrystalline cellulose, from about 10 to about 85 wt. % (e.g., from about 10 to about 50 wt. %) lactose or dibasic calcium phosphate, from about 1 to about 10 wt. % (e.g., from about 1 to about 5 wt. %) croscarmellose sodium, and from about 0.5 to about 10 wt. % (e.g., from about 0.5 to about 3 wt. %) magnesium stearate. In a further aspect of this embodiment, the potassium salt of Compound A in Composition C3 is Form 1 potassium salt of Compound A. In another aspect, Composition C3 is encapsulated or compressed into a tablet. In a feature of this aspect, the capsule or tablet contains the potassium salt of Compound A (e.g., Form 1) in an amount of from about 5 mg to about 900 mg (e.g., from about 5 mg to about 600 mg, or from about 10 mg to about 400 mg).

Unless otherwise indicated, weight percents herein are based on the total weight of all the components in the composition (keeping in mind that, as noted earlier, the weight percent of the drug salt compound is expressed as the weight percent of the parent drug).

As disclosed above, pharmaceutical compositions of the present invention can include a diluent, a disintegrant, and a lubricant. A diluent (also referred to in the art as a "filler") is a substance used to impart bulk to the composition. A diluent can be employed, for example, to provide sufficient bulk to permit the composition to be compressed into a tablet having a practical size. Suitable diluents include anhydrous dibasic calcium phosphate, dibasic calcium phosphate dihydrate, tribasic calcium phosphate, calcium sulfate, carboxymethylcellulose calcium, microcrystalline cellulose, powdered cellulose, glucose, fructose, lactose, mannitol, dextrin, dextrose, dextrates, kaolin, lactitol, magnesium carbonate, magnesium oxide, maltitol, maltodextrin, maltose, starch, sucrose, and talc. In an aspect of the invention, the diluent employed in the pharmaceutical composition of the invention is lactose, microcrystalline cellulose, mannitol, anhydrous dibasic calcium phosphate or dibasic calcum phosphate dihyrate. In another aspect, when the pharmaceutical composition is Composition C1, the diluent is lactose or microcrystalline cellulose. In still another aspect, when the pharmaceutical composition is Composition C1, the diluent is microcrystalline cellulose.

Suitable forms of microcrystalline cellulose for use in pharmaceutical compositions of the invention include, but are not limited to, the materials sold as AVICEL PH-101, AVICEL PH-102, AVICEL PH-103, and AVICEL PH-105 (all of which are available from FMC Corporation), and mixtures thereof. Thus, for example, the microcrystalline cellulose employed in Composition C1 can be AVICEL PH-102 or AVICEL PH-105 or a mixture thereof.

Pharmaceutical compositions of the invention (e.g., compressed tablet compositions and encapsulated granulated compositions) can contain two or more diluents (e.g., microcrystalline cellulose and lactose or dibasic calcium phosphate), which can be employed as a mixture in preparing the composition or can be added separately at the same time or can be added in separate steps in the preparation process (methods for preparing pharmaceutical compositions of the invention are described below). Accordingly, in another aspect of the present invention, the pharmaceutical composition of the present invention comprises a first diluent (e.g., microcrystalline cellulose) and a second diluent (e.g., lactose or dibasic calcium phosphate).

The disintegrant is a substance, or a mixture of substances, employed in the composition to facilitate its breakup or disintegration after administration. Suitable disintegrants include alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, povidone, sodium alginate, sodium starch glycolate, and starch. The disintegrant employed in the pharmaceutical composition of the invention can be a superdisintegrant, such as croscarmellose sodium, crospovidone, or sodium starch glycolate. In an aspect of the invention, when the pharmaceutical composition is Composition C1, the disintegrant is the superdisintegrant croscarmellose sodium.

The lubricant can have one or more functions depending upon the dosage form of the composition. The lubricant can, for example, prevent adhesion of compressed tablets to the compression equipment, it can improve the flow of granules prepared via granulation of the composition prior to their compression or encapsulation, and/or it can improve the flow of an ungranulated powder in the filling of a capsule. Suitable lubricants include calcium stearate, glyceryl monostearate, glyceryl palmitostearate, hydrogenated castor oil, hydrogenated vegetable oil, light mineral oil, magnesium stearate, mineral oil, polyethylene glycol, stearic acid, talc, zinc stearate, and sodium stearyl fumarate. In an aspect of the invention, the lubricant employed in the composition of the invention is magnesium stearate or stearic acid. In another aspect, when the pharmaceutical composition is Composition C1, the lubricant is magnesium stearate.

An antioxidant can be employed in the pharmaceutical composition of the invention to prevent or minimize oxidative degradation of the active ingredient and/or other components of the pharmaceutical composition. Suitable antioxidants include a tocopherol or an ester thereof, an alkyl gallate (e.g., propyl gallate), butylated hydroxyanisole (BHA), butylated hydroxytoluene (BHT), ascorbic acid, sodium ascorbate, citric acid, and sodium metabisulfite. Pharmaceutical compositions of the present invention can, for example, include BHA.

Pharmaceutical compositions of the present invention can be formulated into compressed tablets or capsules. Compressed tablets can be prepared via granulation, wherein the overall particle size of a formulation is increased through the permanent aggregation of smaller particles. Wet or dry granulation can be employed. Wet granulation can be accomplished, for example, by wetting a well-mixed blend of the dry ingredients (e.g., the drug compound salt, anti-nucleating agent, diluent or two diluents, disintegrant, and optionally an antioxidant) with sufficient solvent (e.g., water or water with an alcohol co-solvent) to moisten the dry blend such that particles in the blend tack to one another to form larger particles, and then sieving, comminuting, or otherwise manipulating the size of the particles. Once formed, the resulting wet granulate can then be dried and milled into suitably sized particles (i.e., granules), the granules blended with a lubricant, and the lubricated granules compressed into tablets.

For moisture-sensitive compositions, granulation can be accomplished either by wet granulating with a non-aqueous solvent or by dry granulation. Dry granulation can also be an attractive alternative to wet granulation when the composition is thermally sensitive and subject to degradation at the temperatures employed during the drying of the wet granules. Dry granulation can be accomplished, for example, by dry blending the drug compound salt, the anti-nucleating agent, a first portion of a lubricant and optionally other ingredients (e.g., a diluent and a disintegrant, or two diluents and a disintegrant), and then compressing the blended mixture into slugs or rolling the blended mixture into a compact. The slugs or compact can then be sized (e.g., by passing through a mesh screen or a comminuting mill) to afford the dry granules, which can then be blended with the remaining portion of the lubricant (and optionally, when a diluent or diluents is employed in the blend, an additional amount of the diluent or diluents), and the lubricated granules compressed into tablets.

The compressed tablets can be sugar coated to mask any unpleasant taste or film coated to protect the tablet from atmospheric degradation. Suitable film coating suspensions include combinations of one, two or three of the following components: carboxymethylcellulose sodium, carnauba wax, cellulose acetate phthalate, cetyl alcohol, confectioner's sugar, ethyl cellulose, gelatin, hydroxyethyl cellulose, hydroxypropyl cellulose, hydroxypropyl methylcellulose, liquid glucose, maltodextrin, methyl cellulose, microcrystalline wax, Opadry I and Opadry II, polymethacrylates, polyvinyl alcohol, shellac, sucrose, talc, titanium dioxide, and zein. The films can be applied by spraying the suspension on the tablets and then drying. Film coating techniques and materials suitable for use with the present invention are described in *Remington's Pharmaceutical Sciences*, $18^{th}$ edition, edited by A. R. Gennaro, 1990, Mack Publishing Co., pp. 1665-1675.

Encapsulated pharmaceutical compositions of the present invention can be formed, for example, by dry blending the ingredients of the pharmaceutical composition (i.e., the drug compound salt and the anti-nucleating agent, and optionally one or more other ingredients such as a diluent and/or lubricant), filling capsules (e.g., hard gelatin capsules) with a suitable amount of the blended ingredients, and sealing the capsules. Alternatively, the ingredients can be formed into granules via wet or dry granulation as described above and the capsules filled with a suitable amount of the granules and sealed. The use of granules is preferred when the ungranulated blend has poor bulk flow properties.

Technology and equipment suitable for preparing solid dosage forms of the pharmaceutical compositions of the present invention (e.g., capsules and compressed tablets) are described in *Remington's Pharmaceutical Sciences,* 18th edition, edited by A. R. Gennaro, 1990, Chapter 89.

The present invention includes a process (alternatively referred to herein as "Process P1" or the "P1 process") for preparing a compressed tablet pharmaceutical composition comprising an effective amount of a base salt of a compound of Formula I as defined above, an anti-nucleating agent, a first diluent, a second diluent, a disintegrant, and a lubricant; wherein the method comprises:

(A) blending a mixture of the Compound I base salt, the anti-nucleating agent, none or all or a first portion of the first diluent, the second diluent, the disintegrant, and a first portion of the lubricant;

(B) either (i) compressing the blended mixture to form one or more slugs or (ii) rolling the blended mixture to form a compact, and then sizing the resulting one or more slugs or the resulting compact to form granules;

(C) blending the granules with all or none or the remaining portion of the first diluent and the remaining portion of the lubricant; and (D) compressing the lubricated granules of Step C to obtain the tablet.

Embodiments of the P1 process include the process as just described incorporating one or more of the features (i) to (xiv) as follows:

(i-a) the base salt of Compound I is an alkali metal salt of Compound I;

(i-b) the base salt of Compound I is a sodium salt or a potassium salt of Compound I;

(i-c) the base salt of Compound I is a base salt of Compound A;

(i-d) the base salt of Compound I is an alkali metal salt of Compound A;

(i-e) the base salt of Compound I is a potassium salt of Compound A; or (i-f) the base salt of Compound I is the Form 1 crystalline potassium salt of Compound A;

(ii) the base salt of Compound I is employed in an amount of at least about 5 wt. % (or at least about 10 wt. %, or in a range of from about 5 to about 75 wt. %, or in a range of from about 5 to about 60 wt. %, or in a range of from about 15 to about 50 wt. %);

(iii-a) the anti-nucleating agent is a hydroxyalkylcellulose (e.g., a low-viscosity hydroxyalkylcellulose); or (iii-b) the anti-nucleating agent is HPMC (e.g., a low-viscosity HPMC such as HPMC 2910);

(iv) the anti-nucleating agent is employed in an amount of at least about 0.5 wt. % (or at least about 1 wt. %, or in a range of from about 0.5 to about 20 wt. %, or in a range of from about 1 to about 20 wt. %, or in a range of from about 2 to about 15 wt. %);

(v) the first diluent is microcrystalline cellulose;

(vi) the first diluent is employed in an amount in a range of from about 10 to about 85 wt. % (or from about 15 to about 75 wt. %);

(vii) the second diluent is lactose or dibasic calcium phosphate;

(viii) the second diluent is employed in an amount in a range of from about 10 to about 85 wt. % (or from about 10 to about 50 wt. %);

(ix) the disintegrant is croscarmellose sodium;

(x) the disintegrant is employed in an amount in a range of from about 1 to about 10 wt. % (or from about 1 to about 5 wt. %)

(xi) the lubricant is magnesium stearate;

(xii) the lubricant is employed in an amount in a range of from about 0.5 to about 10 wt. % (or from about 0.5 to about 3 wt. %);

(xiii-a) the process further comprises: (E) coating the compressed tablet; or (xiii-b) the process further comprises: (E) coating the compressed tablet with a film coating suspension to afford a coated tablet in which the coating is from about 1 to about 5% of the weight of the compressed tablet; and (xiv-a) the base salt of Compound I (e.g., potassium salt of Compound A) is employed in a per tablet amount in a range of from about 5 mg to about 1000 mg; or (xiv-b) the base salt of Compound I (e.g., potassium salt of Compound A) is employed in a per tablet amount of about 5 to about 600 mg (e.g., about 100 mg, about 200 mg, about 300 mg, about 400 mg, about 500 mg, or about 600 mg).

Another embodiment of the P1 process is a process for preparing a compressed tablet pharmaceutical composition comprising an effective amount of a potassium salt of Compound A, low viscosity HPMC, microcrystalline cellulose, dibasic calcium phosphate, croscarmellose sodium, and magnesium stearate; wherein the method comprises:

(A) blending a mixture of the Compound A K salt, the HPMC (e.g., HPMC 2910), the dibasic calcium phosphate, croscarmellose sodium, and a first portion of the magnesium stearate;

(B) rolling the blended mixture to form a compact, and then sizing the resulting compact to form granules;

(C) blending the granules with the microcrystalline cellulose (e.g., AVICEL PH-102) and the remaining portion of the magnesium stearate;

(D) compressing the lubricated granules of Step C to obtain the tablet; and (E) optionally coating the compressed tablet with an aqueous film coating suspension (e.g., a suspension of Opadry I).

An aspect of this embodiment is the process as just described incorporating the following features:

(i) the potassium salt of Compound A is employed in an amount of at least about 5 wt. % (or at least about 10 wt. %, or in a range of from about 5 to about 75 wt. %, or in a range of from about 5 to about 60 wt. %, or in a range of from about 15 to about 50 wt. %);

(ii) the HPMC is employed in an amount of at least about 0.5 wt. % (or at least about 1 wt. %, or in a range of from about 0.5 to about 20 wt. %, or in a range of from about 1 to about 20 wt. %, or in a range of from about 2 to about 15 wt. %);

(iii) the microcrystalline cellulose is employed in an amount in a range of from about 10 to about 85 wt. % (or from about 15 to about 75 wt. %);

(iv) the dibasic calcium phosphate is employed in an amount in a range of from about 10 to about 85 wt. % (or from about 10 to about 50 wt. %);

(v) the croscarmellose sodium is employed in an amount in a range of from about 1 to about 10 wt. % (or from about 1 to about 5 wt. %);

(vi) the magnesium stearate is employed in an amount in a range of from about 0.5 to about 10 wt. % (or from about 0.5 to about 3 wt. %); and (vii) the optional coating is from about 1 to about 5% of the weight of the compressed tablet.

The present invention also includes a compressed tablet pharmaceutical composition prepared by the Process P1 as originally set forth above or as set forth in any of the foregoing embodiments of the P1 process.

The present invention includes a process (alternatively referred to herein as "Process P2" or the "P2 process") for preparing a compressed tablet pharmaceutical composition comprising an effective amount of a base salt of a compound of Formula I as defined above, an anti-nucleating agent, a first diluent, optionally a second diluent, a disintegrant, and a lubricant; wherein the method comprises:

(A) wet granulating a mixture of Compound I base salt, the anti-nucleating agent, the first diluent, the optional second diluent, and the disintegrant, and then optionally milling the wet granulated mixture;

(B) drying the wet granulated mixture of Step A;

(C) milling the dried mixture of Step B;

(D) lubricating the milled mixture of Step C with the lubricant; and (E) compressing the lubricated mixture of Step D into a tablet.

Embodiments of the P2 process include the process as just described incorporating one or more of the features (i) to (xiii) as follows:

(i-a) the base salt of Compound I is an alkali metal salt of Compound I;

(i-b) the base salt of Compound I is a sodium salt or a potassium salt of Compound I;

(i-c) the base salt of Compound I is a base salt of Compound A;

(i-d) the base salt of Compound I is an alkali metal salt of Compound A;

(i-e) the base salt of Compound I is a potassium salt of Compound A; or (i-f) the base salt of Compound I is the Form I crystalline potassium salt of Compound A;

(ii) the base salt of Compound I is employed in an amount of at least about 5 wt. % (or at least about 10 wt. %, or in a range of from about 5 to about 75 wt. %, or in a range of from about 5 to about 60 wt. %, or in a range of from about 15 to about 50 wt. %);

(iii-a) the anti-nucleating agent is hydroxyalkylcellulose (e.g., a low-viscosity hydroxyalkylcellulose); or (iii-b) the anti-nucleating agent is HPMC (e.g., a low-viscosity HPMC such as HPMC 2910);

(iv) the anti-nucleating agent is employed in an amount of at least about 0.5 wt. % (or at least about 1 wt. %, or in a range of from about 0.5 to about 20 wt. %, or in a range of from about 1 to about 20 wt. %, or in a range of from about 2 to about 15 wt. %);

(v) the first diluent is microcrystalline cellulose;

(vi) the first diluent is employed in an amount in a range of from about 10 to about 85 wt. % (or from about 15 to about 75 wt. %);

(vii) the optional second diluent is lactose or dibasic calcium phosphate;

(viii) the optional second diluent is employed in an amount in a range of from about 10 to about 85 wt. % (or from about 10 to about 50 wt. %);

(ix) the disintegrant is croscarmellose sodium;

(x) the disintegrant is employed in an amount in a range of from about 1 to about 10 wt. % (or from about 1 to about 5 wt. %)

(xi) the lubricant is magnesium stearate;

(xii) the lubricant is employed in an amount in a range of from about 0.5 to about 10 wt. % (or from about 0.5 to about 3 wt. %); and (xiii-a) the process further comprises: (F) coating the compressed tablet; or (xiii-b) the process further comprises: (F) coating the compressed tablet with a film coating suspension to afford a coated tablet in which the coating is from about 1 to about 5% of the weight of the compressed tablet.

The present invention also includes a compressed tablet pharmaceutical composition prepared by the Process P2 as originally set forth above or as set forth in any of the foregoing embodiments of the P2 process.

The present invention also includes a method for treatment or prophylaxis of a disease or condition in a subject in need of such treatment or prophylaxis, which comprises orally administering as a solid dose a pharmaceutical composition which comprises (i) an effective amount of a drug compound suitable for the treatment or prophylaxis of the disease or condition, wherein the drug compound is in the form of a salt and the salt is characterized by conversion of the drug compound to a less soluble form at a GI-relevant pH (e.g., an acidic pH) above or below its native pH, and (ii) an anti-nucleating agent. This pharmaceutical composition corresponds to the composition as originally defined in the Summary of the Invention. Embodiments of this method include the method as just described wherein the pharmaceutical composition as originally defined is replaced with the above-described embodiments thereof.

The C1, C2 and C3 compositions of the present invention and the compressed tablet compositions prepared by the P1 and the P2 processes are useful in the inhibition of HIV integrase, the treatment or prophylaxis of infection by HIV and the treatment, prophylaxis, or the delay in the onset of consequent pathological conditions such as AIDS. Treating AIDS, the prophylaxis of AIDS, delaying the onset of AIDS, treating HIV infection, or prophylaxis of HIV infection is defined as including, but not limited to, treatment or prophylaxis of a wide range of states of HIV infection: AIDS, ARC, both symptomatic and asymptomatic, and actual or potential exposure to HIV. For example, the compositions of this invention are useful in treating or prophylaxis of infection by HIV after suspected past exposure to HIV by such means as blood transfusion, exchange of body fluids, bites, accidental needle stick, or exposure to patient blood during surgery.

The present invention includes a method for inhibiting HIV integrase in a subject in need thereof which comprises administering to the subject Composition C1 as originally defined above or administering the compressed tablet composition prepared by the P1 or the P2 process as first described above. The invention also includes a method for treating or prophylaxis of HIV infection or for treating, prophylaxis, or delaying the onset of AIDS in a subject in need thereof, which comprises administering to the subject Composition C1 as originally defined above or administering the compressed tablet composition prepared by the P1 or the P2 process as first described above. In these methods, the C1 composition and the P1- and P2-prepared compressed tablet compositions of the present invention can optionally be employed in combination with one or more anti-HIV agents selected from HIV antiviral agents, anti-infective agents, and immunomodulators. Embodiments of these methods include the methods as just described wherein the C1 composition is a C1 composition as set forth in any one of the foregoing embodiments thereof (which include, inter alia, the C2 and C3 compositions) and the compressed tablet composition is a composition resulting from the embodiments of the P1 and P2 processes as set forth above.

The term "subject" (used interchangeably herein with "patient") refers to an animal, preferably a mammal, most preferably a human, who has been the object of treatment, observation or experiment.

When a pharmaceutical composition of the present invention is employed or administered in combination with another agent (e.g., when the C1 composition is administered in combination with an anti-HIV agent), the composition and agent can be administered separately or together, and when administered separately, the composition and agent can be given concurrently or at different times (e.g., alternately).

The present invention also includes a pharmaceutical composition for oral administration as a solid dose, which comprises a drug compound in the form of a salt and an anti-nucleating agent as originally defined and described in the Summary of the Invention (i) for use in, (ii) for use as a medicament for, or (iii) for use in the preparation of a medicament for: treatment or prophylaxis of the disease or condition being treated or prevented by the drug compound. Embodiments of these uses include the uses as just described wherein the pharmaceutical composition as originally defined is replaced with the above-described embodiments thereof.

The present invention also includes Composition C1 of the present invention as originally defined (i) for use in, (ii) for use as a medicament for, or (iii) for use in the preparation of a medicament for: (a) inhibiting HIV integrase, (b) treating or prophylaxis of infection by HUV, or (c) treating, prophylaxis of, or delaying the onset of AIDS. Embodiments of these uses include the uses as just described wherein the C1 composition as originally defined is replaced with the above-described embodiments thereof (which include, inter alia, the C2 and C3 compositions). In these uses, the C1 compositions of the present invention can optionally be employed in combination with one or more anti-IV agents selected from HIV antiviral agents, anti-infective agents, and immunomodulators.

The term "anti-HIV agent" means an agent (other than a compound of Formula I) which is effective in one or more of the following uses: inhibiting integrase or another enzyme required for HIV replication or infection, prophylaxis of HIV infection, treating HIV infection, delaying the onset of AIDS, prophylaxis of AIDS, and treating AIDS.

Suitable HIV antiviral agents for use in combination with Composition C1 include, for example, HIV protease inhibitors (e.g., indinavir, lopinavir optionally with ritonavir, saquinavir, or nelfinavir), nucleoside HIV reverse transcriptase inhibitors (e.g., abacavir, lamivudine (3TC), zidovudine (AZT), or tenofovir), and non-nucleoside HIV reverse transcriptase inhibitors (e.g., efavirenz or nevirapine). These agents can be used in their free form or in the form of pharmaceutically acceptable salts. These agents can also be used per se, but are typically incorporated into suitable pharmaceutical compositions.

The present invention also includes a method for improving the pharmacokinetics of a drug compound orally administered in the form of a salt, wherein the salt is characterized by conversion of the drug compound to a less soluble form at a GI-relevant pH (e.g., an acidic pH) above or below its native pH; wherein the method comprises administering the drug compound salt as a component in a solid-dosage pharmaceutical composition that includes an anti-nucleating agent. An improvement in the pharmacokinetics (PK) of a drug means herein an increase in one or more of the following PK parameters as a result of oral administration of the drug compound salt in a composition with an anti-nucleating agent compared to the corresponding value obtained by oral administration of the drug compound salt in the same manner and using an analogous composition that does not contain the anti-nucleating agent: peak plasma concentration ($C_{max}$), the trough plasma concentration ($C_{min}$), the amount of drug in the bloodstream as measured by the area under the curve of plasma concentration versus time ($AUC_{0-t}$; where t is the time of last sampling, such as 24 hours), and half-life ($T_{1/2}$). Embodiments of this method include the method as just described in which the recited pharmaceutical composition is replaced with embodiments of the pharmaceutical compositions set forth above.

The present invention also includes use of an anti-nucleating agent in a pharmaceutical composition for oral administration as a solid dose, wherein the composition comprises a drug compound in the form of a salt and wherein the salt is characterized by conversion of the drug compound to a less soluble form at a GI-relevant pH (e.g., an acidic pH) above or below its native pH, wherein the use is for improving the PK of the drug compound. The present invention further includes the use of an anti-nucleating agent in a pharmaceutical composition for oral administration as a solid dose, wherein the composition comprises a drug compound in the form of a salt and wherein the salt is characterized by conversion of the drug compound to a less soluble form at a GI-relevant pH (e.g., an acidic pH) above or below its native pH, wherein the use is in the manufacture of a medicament for improving the PK of the drug compound. Embodiments of these uses are analogous to the embodiments for the corresponding method claim.

The pharmaceutical compositions of this invention can be administered in a solid form suitable for oral administration. The compositions can, for example, be administered in the form of capsules or tablets. The compositions can be administered so as to provide the active ingredient in a dosage range of from about 0.001 to about 1000 mg/kg of mammal (e.g., human) body weight per day in a single dose or in divided doses. One preferred dosage range is from about 0.01 to about 500 mg/kg body weight per day in a single dose or in divided doses. Another preferred dosage range is from about 0.1 to about 100 mg/kg body weight per day in single or divided doses.

Composition C1 and embodiments thereof (including, but not limited to, the C2 and C3 compositions) can suitably be provided in the form of tablets or capsules for oral administration, wherein each tablet or capsule contains from about 1 to about 1000 milligrams of the active ingredient, particularly 1, 5, 10, 15, 20, 25, 50, 75, 100, 150, 200, 250, 300, 400, 500, 600, 700, 800, 900 and 1000 milligrams of the active ingredient for the symptomatic adjustment of the dosage to the patient to be treated. In particular, pharmaceutical compositions of the present invention containing a potassium salt of Compound A (e.g., Form 1) are preferably dosed to adult humans as capsules or tablets, wherein the dosage is 100 mg to 600 mg of Compound A twice per day.

The specific dose level and frequency of dosage for any particular patient will depend upon a variety of factors including the activity of the specific drug compound employed, the metabolic stability and length of action of that compound, the age, body weight, general health, sex, diet, mode and time of administration, rate of excretion, drug combination, the severity of the particular condition, and the host undergoing therapy. The appropriate dose level of a particular drug suitable for a particular patient can be determined by the person of ordinary skill in the art without undue experimentation.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —(CH$_2$)$_{1-6}$—, and sub-classes of particular interest include —(CH$_2$)$_{1-4}$—, —(CH$_2$)$_{1-3}$—, —(CH$_2$)$_{1-2}$—, and —CH$_2$—. Also of interest is the alkylene —CH(CH$_3$)—.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms has been replaced with a halogen (i.e., F, Cl, Br and/or I). Thus, for example, "C$_{1-6}$ haloalkyl" (or "C$_1$-C$_6$ haloalkyl") refers to a C$_1$ to C$_6$ linear or branched alkyl group as defined above with one or more halogen substituents. The term "fluoroalkyl" has an analogous meaning except that the halogen substituents are restricted to fluoro. Suitable fluoroalkyls include the series (CH$_2$)$_{0-4}$CF$_3$ (i.e., trifluoromethyl, 2,2,2-trifluoroethyl, 3,3,3-trifluoro-n-propyl, etc.).

The term "aryl" refers to (i) phenyl or (ii) a 9- or 10-membered bicyclic, fused carbocylic ring system in which at least one ring is aromatic. Aryl is typically phenyl or naphthyl, and is more typically phenyl.

The term "HetA" refers to an optionally substituted a 5- or 6-membered heteroaromatic ring containing from 1 to 4 heteroatoms independently selected from N, O and S. In one embodiment, HetA is an optionally substituted heteroaromatic ring selected from the group consisting of pyridinyl, pyrrolyl, pyrazinyl, pyrimidinyl, pyridazinyl, triazinyl, furanyl, thienyl, imidazolyl, pyrazolyl, triazolyl, tetrazolyl, oxazolyl, isooxazolyl, thiazoly, isothiazolyl, and oxadiazolyl; wherein the optional substitution is with 1 or 2 substituents each of which is independently —C$_{1-4}$ alkyl, —C$_{1-4}$ haloalkyl, —O—C$_{1-4}$ alkyl, —O—C$_{1-4}$ haloalkyl, or —CO$_2$—C$_{1-4}$ alkyl. It is understood that HetA can be attached to the rest of the compound of Formula I at any ring atom (i.e., any carbon atom or any heteroatom) provided that a stable compound results.

The term "HetB" refers to an optionally substituted a 5- to 7-membered saturated heterocyclic ring containing from 1 to 4 heteroatoms independently selected from N, O and S. In one embodiment, HetB is an optionally substituted saturated heterocyclic ring selected from the group consisting of pyrrolidinyl, imidazolidinyl, piperidinyl, piperazinyl, morpholinyl, thiomorpholinyl, thiazinanyl, and tetrahydropyranyl, wherein the optional substitution is with 1 or 2 substituents each of which is independently —C$_{1-4}$ alkyl, —C$_{1-4}$ haloalkyl, —C(O)CF$_3$, —C(O)CH$_3$, or —CH$_2$CH$_2$OH. It is understood that HetA can be attached to the rest of the compound of Formula I at any ring atom (i.e., any carbon atom or any heteroatom) provided that a stable compound results. In another embodiment, HetB is selected from the group consisting of

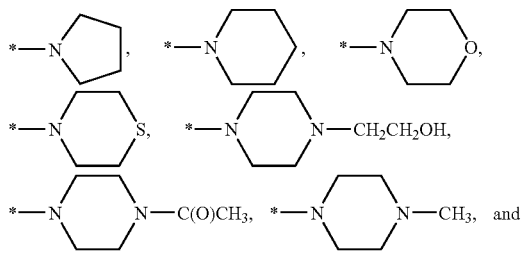

-continued

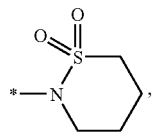

wherein * denotes the point of attachment to the rest of the molecule.

In the compound of Formula I, R$^C$ and R$^D$ together with the nitrogen to which they are attached can form a saturated 5- or 6-membered heterocyclic ring optionally containing a heteroatom in addition to the nitrogen attached to R$^C$ and R$^D$ selected from N, O, and S, where the S is optionally oxidized to S(O) or S(O)$_2$, and wherein the saturated heterocyclic ring is optionally substituted with 1 or 2 C$_{1-6}$ alkyl groups. In one embodiment, the saturated heterocyclic ring formed by R$^C$ and R$^D$ and the nitrogen to which they are attached is selected from the group consisting of 4-morpholinyl, 4-thiomorpholinyl, 1-piperidinyl, 1-piperazinyl optionally substituted with C$_{1-4}$ alkyl (e.g., methyl), and 1-pyrrolidinyl.

Unless expressly stated to the contrary, all ranges cited herein are inclusive. For example, a heterocyclic ring described as containing from "1 to 4 heteroatoms" means the ring can contain 1, 2, 3 or 4 heteroatoms. As another example, a pharmaceutical composition comprising a compound drug salt in a range of from about 5 to about 75 wt. % means the composition can contain about 5 wt. % of the parent drug, about 75 wt. % of the parent drug, or any amount therebetween.

When any variable (e.g., R$^A$ and R$^B$) occurs more than one time in Formula I or in any other formula depicting and describing a compound whose salt can be employed in pharmaceutical compositions of the invention, its definition on each occurrence is independent of its definition at every other occurrence. Also, combinations of substituents and/or variables are permissible to the extent such combinations result in stable compounds.

A "stable" compound is a compound which can be prepared and isolated and whose structure and properties remain or can be caused to remain essentially unchanged for a period of time sufficient to allow use of the compound for the purposes described herein (e.g., use in the form of a salt in a pharmaceutical composition of the invention).

As a result of the selection of substituents and substituent patterns, certain of the compounds of Formula I whose salts can be employed in the present invention can have asymmetric centers and can occur as mixtures of stereoisomers, or as individual diastereomers, or enantiomers. The salts of all isomeric forms of these compounds, whether individually or in mixtures, can be employed in pharamaceutical compositions of the present invention.

Compounds of Formula I can also exist as tautomers due to keto-enol tautomerism. The salts of all tautomers of the hydroxypyrimidinone compounds of Formula I, both singly and in mixtures, can be employed in pharmaceutical compositions of the present invention.

Abbreviations used herein include the following:
ACN=acetonitrile
AIDS=acquired immunodeficiency syndrome
ARC=AIDS related complex
Cbz=benzyloxycarbonyl
DIEA=diisopropylethylamine
DMADC=dimethylacetylene dicarboxylate
DMF=N,N-dimethylformamide
DMSO=dimethylsulfoxide DSC=differential scanning calorimetry
EtOH=ethanol
Eq.=equivalent(s)
GI=gastrointestinal
HIV=human immunodeficiency virus
HPLC=high-performance liquid chromatography
HPMC=hydroxypropylmethylcellulose
IPA=isopropyl alcohol
KF=Karl Fisher titration for water
LC=liquid chromatography
LCAP=LC area percent
LCWP=LC weight percent
Me=methyl
MeOH=methanol
MSA=methanesulfonic acid
MTBE=methyl tertiary butyl ether
MW=molecular weight
NMM=N-methylmorpholine
NMR=nuclear magnetic resonance
PK=pharmacokinetic(s)
TG=thermogravimetric
THF=tetrahydrofuran
XRPD=x-ray powder diffraction The following examples serve only to illustrate the invention and its practice. The examples are not to be construed as limitations on the scope or spirit of the invention.

Example 1

Preparation of Compound A and a Crystalline Potassium Salt Thereof

Step 1: Strecker Amine Formation

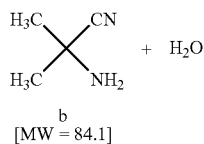

| Material | MW | Eq. | Moles | Mass | Volume | density (g/mL) |
|---|---|---|---|---|---|---|
| acetone cyanohydrin (a) | 85.1 | 1.0 | 129.3 | 11.0 kg | 11.8 L | 0.932 |
| MTBE | | 4.0 | | | 44 L | |
| ammonia (g) | 17.03 | 1.5 | 193.9 | 3.30 kg | 4.9 L | 0.674 |

Acetone cyanohydrin (11.5 kg, 12.3 L) was charged to a 5-gallon autoclave and the vessel placed under 5 psi nitrogen pressure. The autoclave was cooled to 10° C., and ammonia gas (~3.44 kg), pressurized to 30 psi, was fed into the vessel until the reaction reached complete conversion as determined by GC assay (less than 0.5% a). The resulting suspension was transferred to a polyjug and the autoclave rinsed with MTBE (approximately 17 L). The reaction mixture and rinse were then charged to a 100-L extractor followed by MTBE (15 L), the mixture agitated, and the layers carefully separated. The aqueous layer was back-extracted with MTBE (5 L) and the layers carefully separated. The organic layers were combined and charged to a 100 L flask, equipped with a batch concentrator, through an inline filter, and the batch was concentrated (15-20° C., low vacuum) to about 20 L to remove any excess ammonia. The aminonitrile was obtained in 97% assay yield (11.1 kg) by NMR as a solution in MTBE.

Step 2: Addition of Benzyloxycarbonyl (CBz) Protective Group

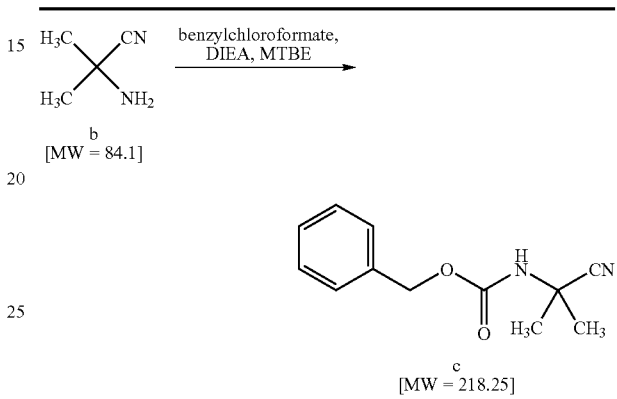

| Material | MW | Eq. | Moles | Mass | Volume |
|---|---|---|---|---|---|
| aminonitrile (b) | 84.1 | | 52.85 | 4.44 assay kg | |
| benzyl-chloroformate | 170.6 | 1.2 | 63.4 | 10.8 kg | |
| DIEA | 129.25 | 1.3 | 68.7 | 8.88 | |
| MTBE | | | | | 62.5 L |

To a visually clean 100-L flask containing a 5-L addition funnel, thermocouple and nitrogen inlet was charged a 59 wt. % solution of cyanoamine b in MTBE (4.44 assay kg). The solution was further diluted with MTBE (62.5 L) to bring the concentration to approximately 15 mL/g. Benzylchloroformate (1.20 equiv, 10.42 kg, 61.10 mol) was then charged in over 15 minutes via the addition funnel at such a rate as to maintain the batch temperature below 35° C. DEEA (1.3 equiv, 8.88 kg, 68.70 mol) was then added over 1.5 hours to the yellow slurry while maintaining the batch temperature below 35° C. The slurry became slightly more soluble as DEA was added but two phases were observed when stirring was stopped. The reaction mixture was aged for 16 hours at 20-25° C., after which DI water (20 L, 4.5 mL/g) was charged into the batch. The batch was then transferred to a 100-L extractor and the phases were separated. The organic layer was then washed with 3×10 L of water and then 15 L of brine. The organic layer was transferred via a 10 μm inline filter to a 100 L round bottom flask and subsequently solvent switched to 90:10 heptane:MTBE. Crystallization occurred during the solvent switch and the resulting white crystalline product was filtered and washed with 3×5 L of 90:10 heptane:MTBE. A total of 10.1 kg of product (88% yield) was obtained in greater than 99 HPLC A %. A total of 26.7 kg of product was obtained in 3 batches with an average isolated yield of 86%.

Step 3: Amidoxime Formation

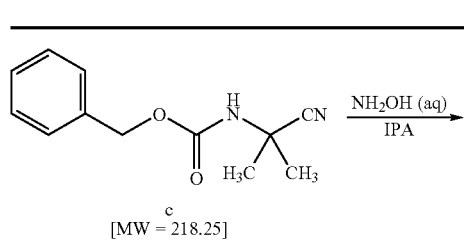

| Material | MW | Eq. | Mass | Volume |
|---|---|---|---|---|
| protected aminonitrile (c) | 218.25 | 1 | 15 g | |
| NH₂OH (50 wt. % in water) | | 1.2 | | 5.05 mL |
| IPA | | | | 40 mL+ |
| | | | | 10 mL |
| n-heptane | | | | 40 mL+ |
| | | | | 50 mL |

A solution of aminonitrile (15 g) in IPA (40 mL) was warmed to 60° C. with stirring and NH₂OH in water (5.05 mL) was added at this temperature over the course of 20 minutes. The clear mixture was then aged at 60° C. for 3 hours, wherein product began to crystallize out of solution at this temperature after 2 hours. The slurry was then cooled to 0°-5° C. and n-heptane (40 mL) was added dropwise over 20 minutes. After stirring for 2 hours at 0°-5° C., the slurry was filtered and the cake was washed with a 20% IPA in heptane solution (60 mL), and then dried under vacuum with a nitrogen stream at room temperature to give pure amide oxime in 88% yield.

Step 4: Formation of Hydroxypyrimidinone

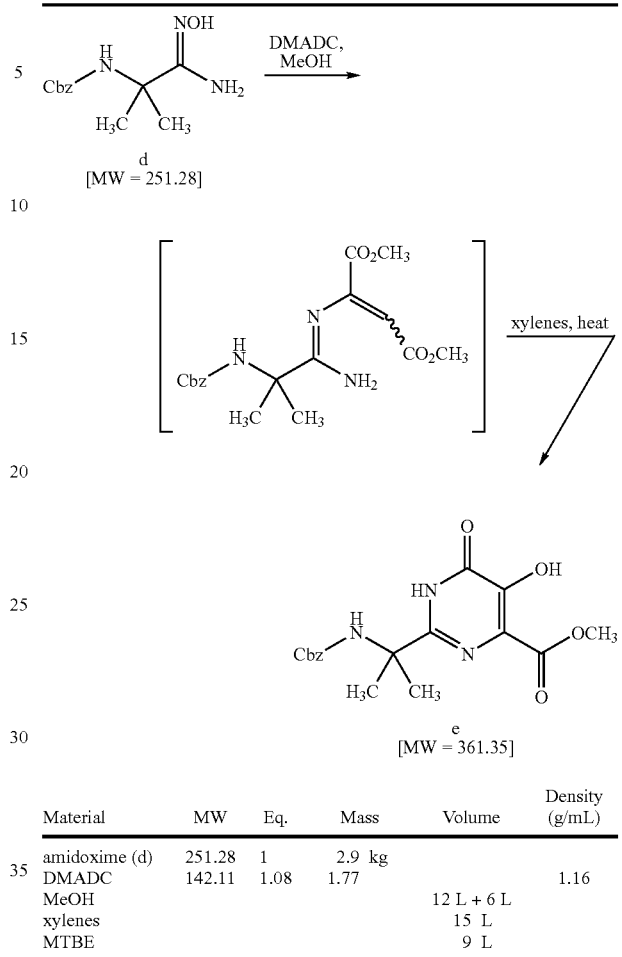

| Material | MW | Eq. | Mass | Volume | Density (g/mL) |
|---|---|---|---|---|---|
| amidoxime (d) | 251.28 | 1 | 2.9 kg | | |
| DMADC | 142.11 | 1.08 | 1.77 | | 1.16 |
| MeOH | | | | 12 L + 6 L | |
| xylenes | | | | 15 L | |
| MTBE | | | | 9 L | |

To a slurry of amidoxime (2.90 kg) in methanol (12 L) was added dimethyl acetylenedicarboxylate (1.77 kg) over 20 minutes. A slow exotherm ensued such that the temperature of the slurry increased from 20° C. to 30° C. over 15-20 minutes. After 1.5 hours, HPLC indicated greater than 95% conversion to the intermediate cis/trans adducts. The solvent was then switched to xylenes under reduced pressure (maximum temperature=50° C.), wherein 2 volumes [2×7.5 L] were added and reduced to a final volume of 7.5 L. The reaction mixture was then heated to 90° C. and kept at this temperature for 2 hours, while flushing the remaining MeOH out with a nitrogen sweep. The temperature was then increased in 10° C. increments over 3.5 hours to 125° C. and held at this temperature for 2 hours. The temperature was then finally increased to 135° C. for 5 hours. The reaction mixture was then cooled to 60° C. and MeOH (2.5 L) was added. After 30 minutes MTBE (9 L) was added slowly to build a seed bed. The batch was then cooled to 0° C. for 14 hours, and then further cooled to −5° C. and aged 1 hour before filtration. The solids were displacement washed with 10% MeOH/MTBE (6 L then 4 L; prechilled to 0° C.) and dried on the filter pot under a nitrogen sweep to afford 2.17 kg (51.7% corrected yield; 99.5 wt %). HPLC method: Column: Zorbax C-8 4.6 mm×250 mm; 40% ACN/60% 0.1% H₃PO₄ to 90% ACN/10% 0.1% H₃PO₄ over 12 minutes, hold 3 minutes then back to 40% ACN over 1 minute. Retention times: amidoxime d—2.4 minutes, DMAD—6.7 minutes, intermediate adducts—8.4 and 8.6 minutes (8.4 minute peak cyclizes faster), product e—5.26 minutes, xylenes—several peaks around 10.4-10.7 minutes.

Step 5: N-Methylation

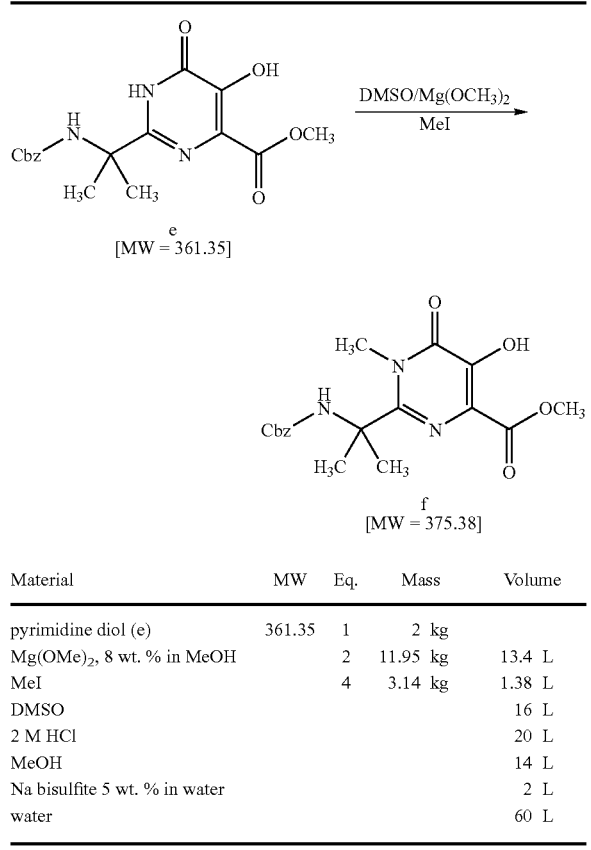

| Material | MW | Eq. | Mass | Volume |
|---|---|---|---|---|
| pyrimidine diol (e) | 361.35 | 1 | 2 kg | |
| Mg(OMe)$_2$, 8 wt. % in MeOH | | 2 | 11.95 kg | 13.4 L |
| MeI | | 4 | 3.14 kg | 1.38 L |
| DMSO | | | | 16 L |
| 2 M HCl | | | | 20 L |
| MeOH | | | | 14 L |
| Na bisulfite 5 wt. % in water | | | | 2 L |
| water | | | | 60 L |

To a solution of the pyrimidine diol e (2 kg) in DMSO (16 L) was added a solution of Mg(OMe)$_2$ in MeOH (11.95 kg), after which excess MeOH was evaporated under vacuum (30 mm Hg) at 40° C. for 30 minutes. The mixture was then cooled down to 20° C., after which MeI (1.38 L) was added and the mixture stirred at 20-25° C. for 2 hours, and then at 60° C. for 5 hours under pressure in a closed flask. HPLC showed that the reaction was complete. The mixture was then cooled to 20° C., after which MeOH (14 L) was added, followed by the slow addition of 2 M HCl (20 L) [exotherm] over 60 minutes. Sodium bisulfite (5 wt. %, 2 L) was then added to quench excess I$_2$, with the solution turning white. Water (40 L) was then added over 40 minutes and the slurry stirred for 40 minutes in an ice bath, and then filtered. The filter cake was washed first with water (20 L) and then with MTBE:MeOH 9/1 (30 L) to remove O-methylated by-product. HPLC showed less than 0.5 A % O-methylated product after washing. The solid was dried overnight at room temperature under vacuum with an N$_2$ stream to give 1.49 kg of N-methyl pyrimidone (70% yield, corrected for purity of starting material and product).

Step 6: Amine Coupling

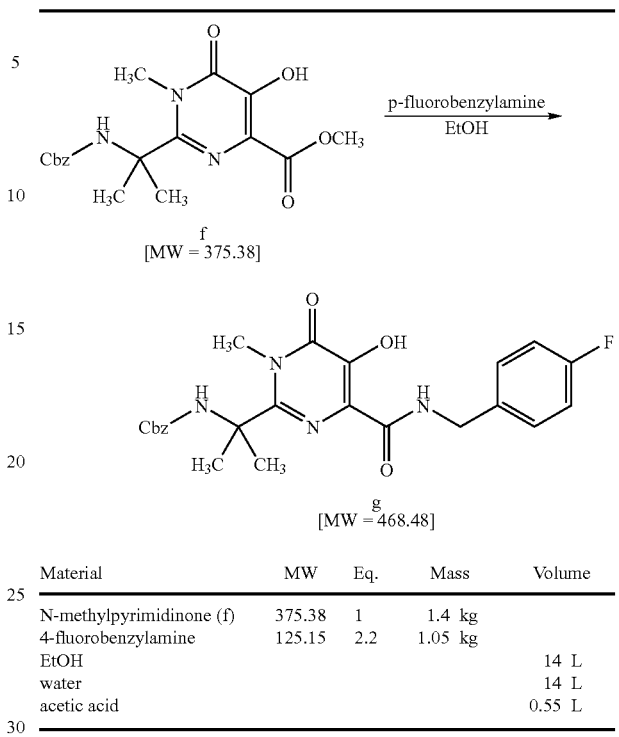

| Material | MW | Eq. | Mass | Volume |
|---|---|---|---|---|
| N-methylpyrimidinone (f) | 375.38 | 1 | 1.4 kg | |
| 4-fluorobenzylamine | 125.15 | 2.2 | 1.05 kg | |
| EtOH | | | | 14 L |
| water | | | | 14 L |
| acetic acid | | | | 0.55 L |

To a slurry of N-methylated pyrimidinone f (1.4 kg) in EtOH (14 L) at 4° C. was slowly added 4-fluorobenzylamine (1.05 kg) over 15 minutes, wherein an exotherm to 9° C. was observed during addition of the first 1 mole equivalent of the amine. The slurry became very thick and vigorous stirring was required. The reaction was warmed to 72° C. over 2 hours and maintained at this temperature for 1 hour and 45 minutes. The solution became extremely viscous at 45° C. where a small exotherm was observed to 50° C., after which the slurry slowly freed up and became homogeneous after 1 hour at 72° C. An HPLC sample assay (HPLC method was similar to that employed in Step 4 above) at the end of the reaction showed less than 0.5 A % N-methylated pyrimidinone. The reaction was then cooled to 60° C. and acetic acid (0.55 L) was added over 30 minutes, followed by the addition of water (6.7 L) over 30 min and then the addition of seed (3.0 g) to initiate crystallization. After 30 min at 60° C., more water (7.3 L) was added over 30 minutes and the reaction mixture allowed to cool to ambient temperature overnight. After 13 hours, the temperature was at 20° C., at which point the reaction mixture was filtered and the slurry washed with 50% water/EtOH (2×4 L). The solids were dried on the filter pot under vacuum/N$_2$ flow to a constant weight to afford a white solid product (1.59 kg; 90% corrected yield; 99% LCWP and 99.7% LCAP as determined by HPLC method similar to that employed in Step 4 above.)

Step 7: Hydrogenation of Cbz-amide

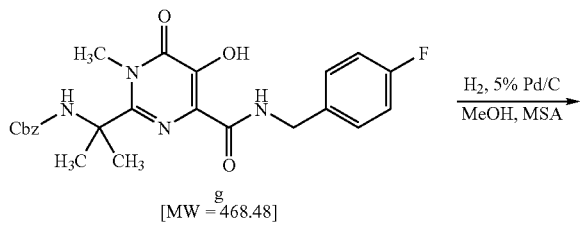 [SMILES: Cn1c(C(C)(C)NC(=O)OCc2ccccc2)nc(C(=O)NCc2ccc(F)cc2)c(O)c1=O]

g
[MW = 468.48]

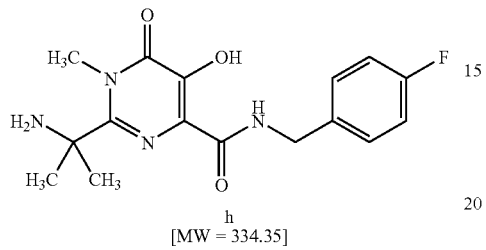

h
[MW = 334.35]

| Material | MW | mmoles | Mass | Volume |
|---|---|---|---|---|
| CBz amide (g) | 468.48 | 21.33 | 10 g | |
| MeOH | | | | 80 mL |
| 5% Pd/C (50% wet) | | | 0.15 g | |
| MSA | 96.1 | 22.4 | | 1.45 mL |
| water | | | | 8 mL |
| cake wash (4:1 MeOH:H₂0) | | | | 20 mL |
| 1 N NaOH | | 22.4 | | 22.4 mL |
| final cake wash (water) | | | | 30 mL |

A stainless steel hydrogenation vessel was preconditioned with MeOH, Pd/C catalyst and MSA under the reaction conditions described below. Cbz-amide g (10 g) was then slurried in MeOH (80 mL) in the preconditioned vessel. MSA (1.45 mL) was added to the slurry in one portion at room temperature. 5% Pd/C (0.15 g, 50% wet) was also added to the hydrogenation vessel. Hydrogen was charged to the vessel in three successive vacuum/hydrogen purge cycles, after which the mixture was hydrogenated at 40 psig for 3-4 hour at 50° C. Following hydrogenation, water (8 mL) was added to the reaction mixture, the mixture was stirred, and the catalyst was filtered and washed with 4:1 MeOH:water (20 mL). The pH of combined filtrates was adjusted to pH 7 to 8.0 by slow addition of 1 N NaOH (22.4 mL), which precipitated a solid. The slurry was stirred at 0-5° C. for 4 hours and the solid filtered, washed with water (30 mL), collected and dried in vacuo at 50° C. The product amine (as hydrate) was obtained as a white crystalline solid (7.7 g) in 96% yield (corrected for KF), 89% LCWP, 99.8% LCAP, KF=11 wt. %

HPLC Method A (product assay): column: 25 cm×4.6 mm Zorbax RX-C8; mobile phase: A=0.1% H₃PO₄, B=CH₃CN, 0 minutes (80% A/20% B), 20 minutes (20% A/80% B), 25 minutes (20% A/80% B); flow: 1.0 mL/minute; wavelength: 210 nm; column temperature: 40° C.; retention times: des-fluoroamine byproduct—5.5 min, amine product—5.85 minutes, toluene—16.5 minutes, Cbz-amide—16.82 minutes.

HPLC Method B (product purity): column: 25 cm×4.6 mm YMC-basic; mobile phase: A=25 mmol KH₂PO₄ adjusted to pH=6.1, B=CH₃CN, 0 minutes (90% A/10% B), 30 minutes (30% A/70% B), 35 minutes (30% A/70% B); flow: 1 mL/minute; wavelength: 210 nm; column temperature: 30° C.; retention times: des-fluoroamine—9.1 minutes, amine—10.1 minutes, toluene—24.2 minutes, Cbz amide—25.7 minutes.

Step 8: Oxadiazole Coupling
Part A: Preparation of Oxadiazole K Salt

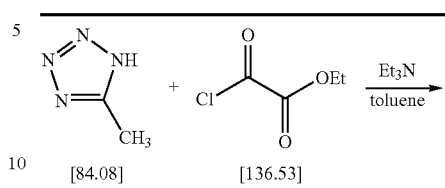

[84.08]    [136.53]

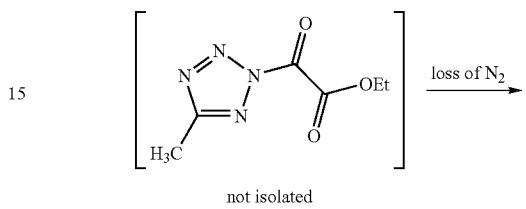

not isolated

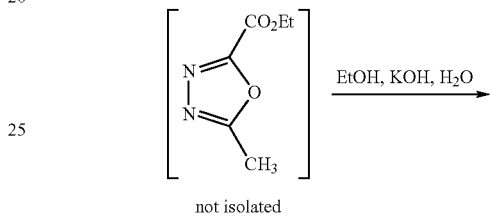

not isolated

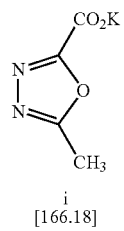

i
[166.18]

| Material | Eq. | Mole | Mass | Volume | Density |
|---|---|---|---|---|---|
| 5-methyltetrazole (96 wt. %) | 1.0 | 28.54 | 2.5 kg (2.4 kg) | | |
| ethyloxalyl chloride | 1.03 | 29.4 | 4.014 kg | 3.29 L | 1.22 |
| triethylamine | 1.05 | 29.97 | 3.033 kg | 4.21 L | 0.72 |
| toluene | | | | 74 L | |
| EtOH (punctilious) | | | | 61 L | |
| MTBE | | | | 15 L | |
| KOH aq. *20 wt. % | | | | 8 L | |
| 10% brine | | | | 5 L | |

Ethyl oxalylchloride (4.01 kg) was slowly added to a mixture of 5-methyltetrazole (2.50 kg), triethylamine (3.03 kg) in toluene (32 L) at 0° C. at such a rate that the temperature stays below 5° C. The resulting slurry was stirred for 1 hour at 0-5° C. then the triethylamine/HCl salt was filtered off. The solid was washed with 27 L of cold toluene (5° C.). The combined filtrates were kept at 0° C. and were slowly added to a hot solution of toluene (50° C., 15 L) over 40-50 minutes (N₂ gas evolution), then the solution was aged at 60-65° C. for 1 hour. After cooling at 20° C., the toluene solution was washed with 5 L of 10% brine, then solvent switched to ethanol (reduced to 8 L, then 17 L of EtOH was added, then concentrated down to 8 L, then 33 liters of EtOH were added to adjust final volume of 41 L). The ethanol solution was cooled to 10° C. and KOH aq. (8.0 L) was added over 30 minutes, and the resulting thick slurry was then stirred for 40 minutes at room temperature while the oxadiazole K salt crystallized out. The solid was filtered off, washed with 11 L of EtOH and finally with 15 L of MTBE. The solid was dried overnight under vacuum at 20° C. with a nitrogen stream to yield 4.48 kg (90.8%) of the K-salt i.

Part B: Oxadiazole Coupling

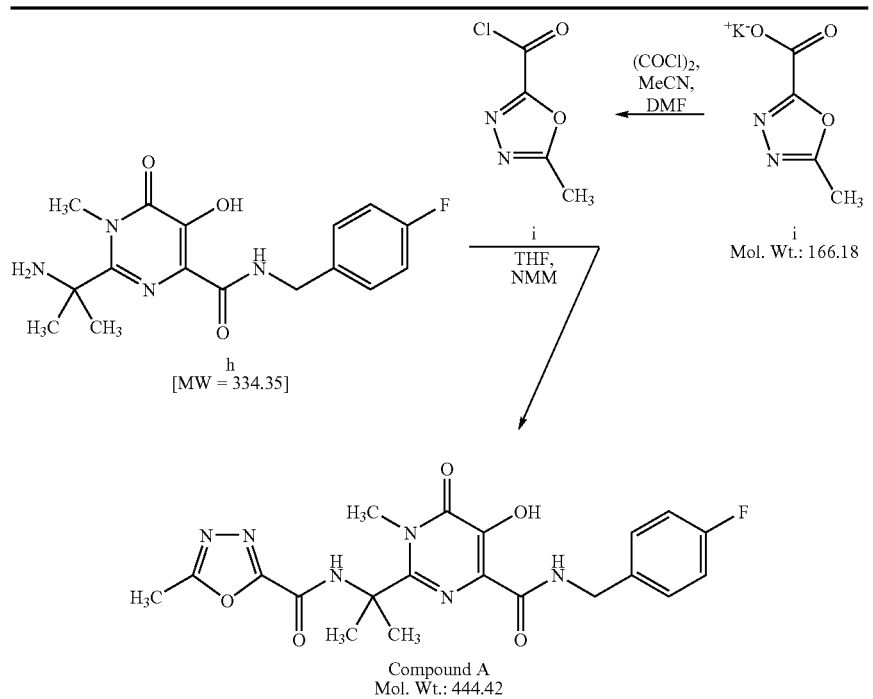

Compound A
Mol. Wt.: 444.42

| Reagent | Mass | mL | Moles | Eq. |
|---|---|---|---|---|
| oxadiazole K salt i | 33.8 g (96.1 wt %) | | 0.20 | 2.2 |
| ACN | | 280 mL | | |
| DMF | 0.33 | | | |
| oxalyl chloride | 23.7 g | 16.3 mL | 0.19 | 2.1 |
| free amine h | 30 g (99 wt %) | | 0.089 | 1 |
| THF | | 821 mL | | |
| NMM | 21.56 g | 23.4 mL | 0.21 | 2.4 |
| NH$_4$OH (30% in H$_2$O) | 62.3 g | 69 mL | 0.53 | 6 |
| HCl (2 N) | | 500 mL | | |
| IPA | | 920 mL | | |
| water | | 400 mL | | |
| MeOH | | 300 mL | | |

A 500 mL round bottom flask was charged with oxadiazole K salt i (33.8 g) followed by ACN (280 mL) and DMF (0.33 mL) with strong stirring. The resulting slurry was then cooled down to 0-5° C. and oxalyl chloride (23.7 g) was added over the course of 20 minutes in order to maintain the internal temperature at less than 5° C. The resulting acyl chloride-containing slurry was then aged for 1 hour.

To a 2 L round bottom flask the free amine h (30 g) was added followed by THF (821 mL). The resulting slurry was cooled down to 0-5° C., after which NMM (21.56 g) was added and the slurry so obtained was stirred for 10 minutes at the cold temperature. The previously prepared acyl chloride-containing slurry was added slowly to the free amine slurry over the course of 20 minutes such that the temperature did not exceed 5° C. The slurry was then aged for 1.5 hours at 0-5° C. At this time HPLC showed no more amine h (<0.5% LCAP, 100% conversion). The reaction mixture was then quenched with NH$_4$OH (30% in water) (69 mL) which was added over the course of 3 minutes. The resulting yellow slurry was then stirred for an additional hour at temperatures less than 10° C. The yellow slurry was then acidified to pH 2-3 with HCl (2N) (500 mL). To the resulting red wine colored solution, IPA (920 mL) was added. The low boiling point organic solvents were then evaporated under reduced pressure (40 torr) at room temperature to a final solution volume of 1100 mL, at which volume crystalline Compound A began to precipitate. Water (400 mL) was then added to this new slurry over the course of 10 minutes, and the slurry aged overnight at room temperature. The aged slurry was filtered and the solid obtained was washed with water (170 mL), followed by a swish wash with cold MeOH (300 mL, previously cooled in an ice bath), and finally by a swish wash with water (700 mL). The solid so obtained was dried overnight under vacuum and nitrogen stream to give 35.5 g of Compound A (91% yield).

Step 9: Formation of a Crystalline Potassium Salt of Compound A

Acetonitrile (50 mL) and anhydrous Compound A (5.8 g, 97.4 wt. %) were charged at room temperature to a jacketed 125 mL round bottom flask equipped with a mechanical stirrer and equipped with a nitrogen inlet (i.e., the crystallization was conducted under nitrogen). The resulting slurry was agitated at 45° C. until the solids were completely in solution. Form 1 crystalline Compound A K salt was then charged to the solution as seed (0.184 g, 3 wt % to theoretical K salt). Aqueous KOH 30% w/v solution (0.98 eq., 2.33 mL, 0.0125 moles) was then added with the following charge profile while maintaining batch at 45° C.:

0.466 mL over 5 hours, 0.0932 mL/hr (20 mol %)
1.864 mL over 7 hours, 0.2663 mL/hr (80 mol %)

The resulting slurry was cooled to 20° C. and aged at 20° C. until the concentration of Compound A in the mother liquor was measured to be less than 4 g/L. The batch was filtered, the cake washed with ACN (3×12 mL), and then dried under vacuum at 45° C., with a small nitrogen sweep, until the amount of ACN and water present as determined by thermogravimetric analysis was less than 1 wt. %. The K salt of Compound A was obtained in >99 A % by HPLC analysis.

Example 2

Form 1 Crystalline Potassium Salt of Compound A

Part A: Preparation

Ethanol (147 mL), water (147 mL), and Compound A (97.9 g assay by HPLC) were charged to a 1 L round bottom flask equipped with mechanical stirrer, addition funnel, nitrogen inlet (i.e., run conducted under nitrogen), and a thermocouple. Aqueous KOH (45% w/w, 0.98 eq., 18.5 mL, 216 mmoles) was added to the suspension over 10 minutes at 21° C. The resulting suspension was agitated for 0.5 hour resulting in the dissolution of a majority of the solids, after which the batch was filtered through a 1 μm filter directly into a 5 L round bottom flask equipped with mechanical stirrer, addition funnel, nitrogen inlet, and thermocouple. The 1 L flask was rinsed with 1:1 (v/v) water/EtOH (48 mL) and the rinse was filtered into the 5 L crystallization vessel. The filtered solution was seeded with crystalline Form 1 Compound A K salt (200 mg) at room temperature and then aged for 1 hour to build a good seed bed, after which the suspension was diluted with EtOH (1.57 L) at 20° C. over 1.5 hour The batch was then cooled to about 4° C. and aged until the concentration of Compound A in the mother liquor was measured to be 4.7 g/L. The batch was filtered, the crystallization vessel rinsed with 50 mL EtOH into the filter, the cake washed with EtOH (4×100 mL), and then dried under vacuum and a nitrogen tent until the amount of EtOH present by NMR was about 0.4 mol % relative to the potassium salt. The potassium salt of Compound A was obtained in 88% yield (91.5 g assay by HPLC, 99 area % by HPLC analysis).

Part B: Characterization

An XRPD pattern of a K salt prepared in the manner described in Part A was generated on a Philips Analytical X'Pert Pro X-ray powder diffractometer using a continuous scan from 2.5 to 40 degrees 2Θ over about 12 minutes (i.e., 0.02° step size with 40 seconds/step), 2 RPS stage rotation, and a gonio scan axis. Copper K-Alpha I ($K_{\alpha 1}$) and K-Alpha 2 ($K_{\alpha 2}$) radiation was used as the source. The experiment was run under ambient conditions. Characteristic 2Θ values in the XRPD pattern (shown in FIG. 1) and the corresponding d-spacings include the following:

| Peak No. | d-spacing (Å) | 2 Theta |
| --- | --- | --- |
| 1 | 14.9 | 5.9 |
| 2 | 7.1 | 12.5 |
| 3 | 4.4 | 20.0 |
| 4 | 4.3 | 20.6 |
| 5 | 3.5 | 25.6 |

Figure 2:
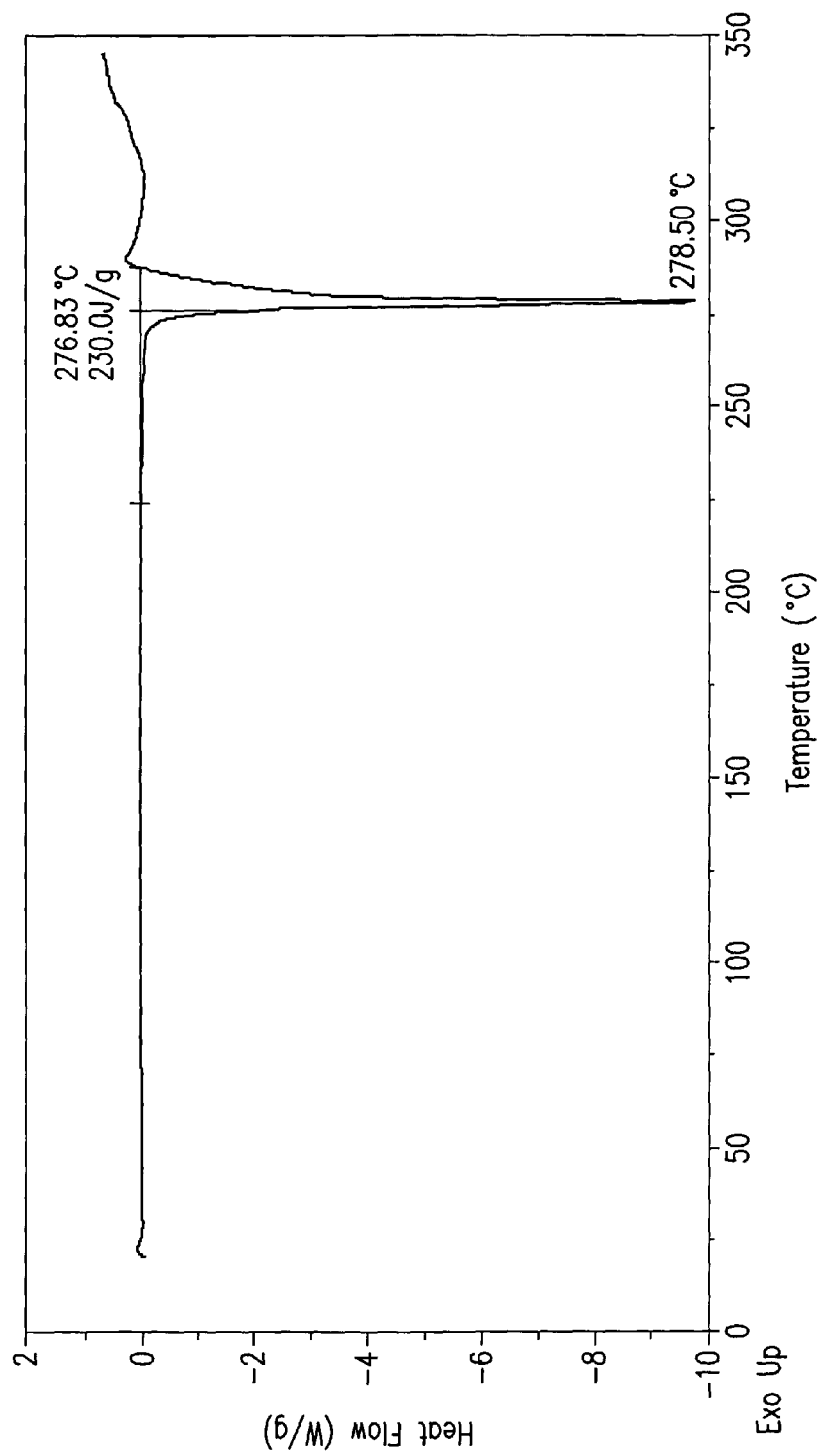
FIG. 2 is the DSC curve for the potassium salt of Compound A as prepared in Example 2.

A K salt prepared in the manner described in Part A was also analyzed by a TA Instruments DSC 2910 differential scanning calorimeter at a heating rate of 10° C./min from room temperature to 350° C. in a crimped pinhole aluminum pan in a nitrogen atmosphere. The DSC curve (shown in FIG. 2) exhibited a single, sharp endotherm with a peak temperature of about 279° C. and an associated heat of fusion of about 230.0 J/gm. The endotherm is believed to be due to melting.

A thermogravimetric analysis was performed with a Perkin-Elmer Model TGA 7 under nitrogen at a heating rate of 10° C./min from room temperature to about 350° C. The TG curve showed a 0.3% weight loss during heating to 250° C.

Hygroscopicity data was obtained on a VTI Symmetrical Vapor Sorption Analyzer Model SGA-1. Data was collected at room temperature from 5-95% relative humidity and back, 5% relative humidity change per step. Equilibrium conditions were 0.01 weight percent change in 5 minutes with a maximum equilibration time of 180 minutes. The data indicated that the material had a 1.8% weight increase when equilibrated at 95% RH at 25° C. When equilibrated back down to 5% RH, the material returned back to approximately its dry weight. An XRPD analysis of the material after the hygroscopicity experiment showed that the material had not changed phases.

K salt prepared as described in Part A was also assayed by HCl titration using a Brinkmann Metrohm 716 DMS Titrino. The assay results indicated the salt was a monopotassium salt.

Example 3

Preparation of Compressed Tablets Containing Compound a Potassium Salt

Part A—

| Ingredient | Amount per Tablet (mg) | Amt per batch (wt. percent) |
| --- | --- | --- |
| Compound A K salt[1] | 111.2 | 27.8 |
| (on free phenol basis) | (100) | (25.0) |
| microcrystalline cellulose (AVICEL PH-102) | 189.6 | 47.4 |
| lactose monohydrate | 63.2 | 15.8 |
| croscarmellose sodium | 12.0 | 3.0 |
| HPMC 2910 (6 centipoise) | 20.0 | 5.0 |
| magnesium stearate (intragranular) | 2.0 | 0.5 |
| magnesium stearate (extragranular) | 2.0 | 0.5 |

[1]Form 1 crystalline monopotassium salt of Compound A; conversion factor (including purity) = 1.112.

Compressed tablets containing 100 mg of Compound A on a free phenol basis were prepared by blending all of the ingredients listed above, except for the extragranular magnesium stearate, in a blender (Turbula® Type T2F shaker-mixer, Basel, Switzerland) for 10 minutes. Portions of the blended material weighing approximately 1 gram were compressed into compacts (or slugs) in a benchtop press (Auto Carver Model Auto "C", Catalog No. 3888, Carver, Inc., Wabash, Ind.) using 1×0.5 inch rectangular tooling to 12 MPa (4 KN). The slugs were then sized into granules by passing them through a sieve with 1 mm openings. The granules were blended with the extragranular magnesium stearate in the Turbula blender for 5 minutes, and the lubricated granules were compressed into tablets using the Auto Carver press with 13/32-inch standard concave round tooling. Tablets employed in the pharmacokinetic studies described below (see Example 5) were prepared by compressing with a force to 15 KN, and tablets for the in vitro dissolution study (see Example 4) were prepared by compressing to forces in a range from 5 to 15 KN.

Tablets of the same size but containing 10 wt. % and 15 wt. % HPMC (v. 5 wt. % HPMC) were prepared in the manner described in the preceding paragraph for the in vitro dissolution study, wherein the amounts of lactose and microcrystalline cellulose were reduced to 14.6 and 12.8 wt. % and 43.9 and 38.4 wt. % respectively to accommodate the additional HPMC. In addition, tablets of the same size but containing no HPMC (i.e., "reference" tablets) were also prepared in the manner described in the preceding paragraph for the in vitro dissolution study, wherein the amounts of lactose and microcrystalline cellulose were increased to 17.1 and 51.2 wt. % respectively to compensate for the absence of HPMC.

Part B—

| Ingredient | Amount per Tablet (mg) | Amt per batch (wt. percent) |
|---|---|---|
| Compound A K salt[1] | 110 | 27.5 |
| (on free phenol basis) | (100) | (25.0) |
| microcrystalline cellulose (AVICEL PH-102) | 175.2 | 43.8 |
| microcrystalline cellulose (AVICEL PH-105) | 9.2 | 2.3 |
| lactose monohydrate | 61.6 | 15.4 |
| croscarmellose sodium | 12.0 | 3.0 |
| HPMC 2910 (6 centipoise) | 20.0 | 5.0 |
| magnesium stearate (intragranular) | 4.0 | 1.0 |
| magnesium stearate (extragranular) | 8.0 | 2.0 |

[1]Form 1 crystalline monopotassium salt of Compound A; conversion factor (including purity) = 1.112.

Compressed tablets having the composition set forth in the above table were prepared using a procedure similar to that set forth in Part A.

Example 4

In Vitro Dissolution Study

The dissolution properties of tablets prepared in the manner described in Part A of Example 3 (i.e., tablets containing 100 mg of Compound A on a free phenol basis and 0, 5, 10 or 15 wt. % HPMC) were tested in the following manner: Two tablets containing 0, 5, 10, or 15 wt. % HPMC were added to a USP Type II dissolution vessel containing 500 mL of 0.01 N HCl (pH=2) as the dissolution medium (ambient temperature). After the tablets were allowed to sink to the bottom of the vessel, the medium was stirred at 100 rpm for 60 minutes and then at 150 rpm for up to an additional 120 minutes. Samples (5 mL) were removed from medium at 5, 10, 15, 20, 30, 60, 90 and 120 minutes and at the conclusion of the test (180 minutes). Each sample was diluted 1:1 with 50:50 (volume:volume) acetonitrile:water, and then analyzed via HPLC or W spectrophotometry to determine the concentration of Compound A in the solution. (Note: The HPLC and UV methods were determined to be equivalent; the choice of method for a particular test was based on such factors as equipment availability.)

HPLC: column=Agilent Zorbax RX-C8; mobile phase=60:40 (v:v) 0.1% $H_3PO_4$:ACN; flow rate=1.5 mL/minute; column temperature=ambient; injection volume=20 µL; detection wavelength=303 nm; run time=5 minutes.

UV: sampling=sipper with 25 second pump time and 3 second wait time; path length=1 mm; wavelength=303 nm.

Tablets containing HPMC showed prolonged drug supersaturation relative to the reference tablets containing no HPMC, wherein drug concentrations for the HPMC-containing tablets at dissolution times of 120 and 180 minutes were at least 2-fold greater than achieved for the reference tablets. Tablets with 10 wt. % and 15 wt. % HPMC exhibited slower disintegration in the dissolution vessel and slower drug release than the tablets containing 5 wt. % HPMC, but nonetheless achieved prolonged supersaturation as well.

In vitro dissolution studies similar to the study described above, but conducted with unformulated bulk Compound A K salt and formulated bulk in granules and conducted at 37° C. (physiological temperature) showed a more pronounced and favorable effect of HPMC, even at a level of HPMC equivalent to 2.5 wt. % A 10-fold enhancement in drug solubility was observed at dissolution times of 60 to 180 minutes for dissolution of the formulated and unformulated bulk drug in the presence of HPMC versus dissolution in the absence of HPMC.

Example 5

Pharmacokinetic Study

Pharmacokinetic (PK) values for Compound A were determined in Beagle dogs orally dosed with compressed tablets prepared in the manner described in Part A of Example 3 and containing 100 mg of Compound A K salt (free phenol basis) and 5 wt. % HPMC. Male, purpose-bred beagle dogs (Marshall Farms) were used in all the studies. The dogs were housed in an AAALAC-accredited facility in accordance with USDA guidelines. Studies were conducted under a protocol approved by the WP-IACUC. Dog weights were measured and recorded prior to dosing. Dog weights ranged from approximately 8 to 10 kg. Dogs having similar weights were employed in each of the studies. Three or four dogs were employed in each study. The dose was approximately 10 mg per kg of body weight (i.e., 10 mpk).

Dosing:

Following an overnight fast all dogs were treated subcutaneously with pentagastrin (0.064 mg/kg, 0.1 mL/kg) approximately a half hour prior to dosing. The dogs were orally administered tablet formulations followed by 5 mL/kg of water. Water was returned at 2 hours after dosing and food was returned 4 hours after dosing. Blood was drawn from 21 gauge catheters placed in the cephalic vein at pre-dose, and 0.25, 0.5, 1, 1.5, 2, 3, 4, 6, 8 and 24 hours after dosing. The plasma was separated by centrifugation (15 minutes at 2500 g) and stored overnight at −70° C. for LC/MS/MS the following day.

Sample Preparation and Analysis:

The plasma samples were extracted using solid phase extraction. Plasma extracts were injected onto a Waters Xterra MS C18, 2×50 mm, 5 µm HPLC column and analyzed using a 4.61-minute gradient consisting of 0.1% formic acid in water and 0.1% formic acid in acetonitrile. The sample extracts were ionized using a TurbolonSpray interface and were monitored by selected reaction monitoring (SRM) in the positive ionization mode. The dynamic range of the LC/MS/MS assay was 5-8000 ng/mL based on a 50 µL aliquot of dog plasma.

PK Calculations:

Area under the curve for a plot of plasma concentration v. time to last sampling ($AUC_{0-24}$ hrs), observed maximum plasma concentration ($C_{max}$), and time of $C_{max}$ ($T_{max}$) were calculated using a linear trapezoidal, non-compartmental model of WinNonLin v 3.1. Means and SD were calculated using Excel® 97 SR-2(f). Plasma profiles were generated using SigmaPlot v. 8.0 for Windows.

Analogous PK studies were done with a 5 wt. % methylcellulose aqueous solution of the Compound A K salt, a dry-filled capsule of bulk drug ("DFC"), and the reference tablet containing no HPMC prepared as described in Example 3. The data showed a 2-fold improvement in $AUC_{0-24}$ hrs for the HPMC-containing tablet compared to the $AUC_{0-24}$ hrs values obtained for the reference tablet and the dry-filled capsule. The AUC$_{0-24}$ hrs of the HPMC-containing tablet was equivalent to that of the methylcellulose solution.

Example 6

Preparation of Film-Coated Compressed Tablets Containing Compound A Potassium Salt

| Ingredient | Amount per Tablet (mg) | Amt per batch (wt. percent) |
|---|---|---|
| Compound A K salt[1] | 434.4 | 54.3 |
| (on free phenol basis) | (400) | (50.0) |
| microcrystalline cellulose (AVICEL PH-102; extragranular) | 187.7 | 23.5 |
| lactose monohydrate | 93.9 | 11.7 |
| croscarmellose sodium | 24.0 | 3.0 |
| HPMC 2910 (6 centipoise) | 40.0 | 5.0 |
| magnesium stearate (intragranular) | 6.0 | 0.75 |
| magnesium stearate (extragranular) | 14.0 | 1.75 |
| Opadry White 20A 18273 (film coating) | 16.0[2] | 4.0[2] |

[1]Form 1 crystalline monopotassium salt of Compound A; conversion factor = 1.086.
[2]Target weight gain during film coating with respect to the core tablet.

Compressed tablets containing 400 mg of Compound A on a free phenol basis were prepared by blending all of the ingredients listed above, except for the extragranular microcrystalline cellulose, magnesium stearate and Opadry White, in a blender (Patterson-Kelly V blender; hereinafter the "V-blender") for 10 minutes, followed by lubrication for 5 minutes with intragranular magnesium stearate in the same blender. The blend was then roller compacted into ribbons in an Alexanderwerk WP 120 roller compactor using a 25 mm knurled roll at 60 bar roll pressure. The ribbons were subsequently milled into granules using the rotary fine granulator (an integral part of the WP 120 roller compactor) equipped with 2.0 mm and 0.8 mm size screens. The granules were then blended with extragranular microcrystalline cellulose in the V-blender for 10 minutes, followed by 5 minutes lubrication with the extragranular magnesium stearate in the same blender. The lubricated granules were then compressed on a rotary tablet press (Korsch) to 800 mg image tablets using 2×16/32" standard round concave tooling. The hardness of the core tablets was measured to be between 10 to 15 kiloponds (kp=1 kgf). The core tablets were then coated with Opadry White in a Vector film coater (1.3 L pan) to afford film-coated tablets with approximately a 4% weight gain with respect to the core tablet.

Example 7

Preparation of Film-Coated Compressed Tablets Containing Compound A Potassium Salt Compressed tablets having the following composition were prepared in accordance with the procedure described in Example 6:

| Ingredient | Amount per Tablet (mg) | Amt per batch (wt. percent) |
|---|---|---|
| Compound A K salt[1] | 434.4 | 54.3 |
| (on free phenol basis) | (400) | (50.0) |
| microcrystalline cellulose (AVICEL PH-102; extragranular) | 141.8 | 17.725 |
| dibasic calcium phosphate | 141.8 | 17.725 |

-continued

| Ingredient | Amount per Tablet (mg) | Amt per batch (wt. percent) |
|---|---|---|
| croscarmellose sodium | 24.0 | 3.0 |
| HPMC 2910 (6 centipoise) | 40.0 | 5.0 |
| magnesium stearate (intragranular) | 8.0 | 1.0 |
| magnesium stearate (extragranular) | 10.0 | 1.25 |
| Opadry White 20A 18273 (film coating) | 16.0[2] | 4.0[2] |

[1]Form 1 crystalline monopotassium salt of Compound A; conversion factor = 1.086.
[2]Target weight gain during film coating with respect to the core tablet.

While the foregoing specification teaches the principles of the present invention, with examples provided for the purpose of illustration, the practice of the invention encompasses all of the usual variations, adaptations and/or modifications that come within the scope of the following claims.

What is claimed is:

1. A pharmaceutical composition for oral administration as a solid dose, which comprises: (a) from 2 to 15 wt. % of an anti-nucleating agent which comprises a hydroxyalkylcellulose, and (b) from 5 to 75 wt. % of a potassium salt of Compound A, wherein Compound A is:

2. The pharmaceutical composition according to claim 1, wherein the potassium salt of Compound A is Form 1 potassium salt of Compound A.

3. The pharmaceutical composition according to claim 1, wherein the anti-nucleating agent comprises hydroxypropylmethylcellulose.

4. The pharmaceutical composition according to claim 1, which further comprises a first diluent, a second diluent, a disintegrant, and a lubricant.

5. The pharmaceutical composition according to claim 4, wherein:
the anti-nucleating agent is hydroxypropylmethylcellulose;
the first diluent is microcrystalline cellulose;
the second diluent is lactose or dibasic calcium phosphate;
the disintegrant is croscarmellose sodium; and
the lubricant is magnesium stearate.

6. The pharmaceutical composition according to claim 5, wherein:
the microcrystalline cellulose is employed in an amount of from 10 to 85 wt. %;
the lactose or dibasic calcium phosphate is employed in an amount of from 10 to 85 wt. %;
the croscarmellose sodium is employed in an amount of from 1 to 10 wt. %; and
the magnesium stearate is employed in an amount of from 0.5 to 10 wt. %.

7. The pharmaceutical composition according to claim 6, wherein the potassium salt of Compound A is Form 1 potassium salt of Compound A.

8. The pharmaceutical composition according to claim 6, wherein the composition is encapsulated or compressed into a tablet.

9. The pharmaceutical composition according to claim 8, wherein the potassium salt of Compound A is employed in an amount of from 5 mg to 900 mg.

10. A process for preparing a compressed tablet having a pharmaceutical composition according to claim 4, wherein the method comprises:
(A) blending a mixture of the Compound A potassium salt, the anti-nucleating agent, none or all or a first portion of the first diluent, the second diluent, the disintegrant, and a first portion of the lubricant;
(B) either (i) compressing the blended mixture to form one or more slugs or (ii) rolling the blended mixture to form a compact, and then sizing the resulting one or more slugs or the resulting compact to form granules;
(C) blending the granules with all or none or the remaining portion of the first diluent and the remaining portion of the lubricant; and
(D) compressing the lubricated granules of Step C to obtain the tablet.

11. The process according to claim 10, wherein:
the anti-nucleating agent is hydroxypropylmethylcellulose;
the first diluent is microcrystalline cellulose;
the second diluent is lactose or dibasic calcium phosphate;
the disintegrant is croscarmellose sodium; and
the lubricant is magnesium stearate.

12. The process according to claim 11, wherein:
the microcrystalline cellulose is employed in an amount of from 10 to 85 wt. %;
the lactose or dibasic calcium phosphate is employed in an amount of from 10 to 85 wt. %;
the croscarmellose sodium is employed in an amount of from 1 to 10 wt. %; and
the magnesium stearate is employed in an amount of from 0.5 to 10 wt. %.

13. A process for preparing a compressed tablet having a pharmaceutical composition according to claim 4, wherein the method comprises:
(A) wet granulating a mixture of Compound A potassium salt, the anti-nucleating agent, the first diluent, the second diluent, and the disintegrant, and then optionally milling the wet granulated mixture;
(B) drying the wet granulated mixture of Step A;
(C) milling the dried mixture of Step B;
(D) lubricating the milled mixture of Step C with the lubricant; and
(E) compressing the lubricated mixture of Step D into a tablet.

14. A method for improving the pharmacokinetics of a compound of Formula I as recited in claim 1 orally administered in the form of a base salt, wherein the method comprises administering the compound base salt as a component in a solid-dosage pharmaceutical composition that includes an anti-nucleating agent.

15. A method for the treatment of HIV infection in a subject in need thereof which comprises administering to the subject the pharmaceutical composition according to claim 1.

16. The pharmaceutical composition according to claim 6, wherein:
the potassium salt of Compound A is employed in an amount of from 5 to 60 wt. %;
the microcrystalline cellulose is employed in an amount of from 15 to 75 wt. %;
the lactose or dibasic calcium phosphate is employed in an amount of from 10 to 50 wt. %;
the croscarmellose sodium is employed in an amount of from 1 to 5 wt. %; and
the magnesium stearate is employed in an amount of from 0.5 to 3 wt. %.

17. The pharmaceutical composition according to claim 16, wherein the composition is encapsulated or compressed into a tablet.

18. The pharmaceutical composition according to claim 16, wherein the potassium salt of Compound A is Form 1 potassium salt of Compound A.

19. The pharmaceutical composition according to claim 18, wherein the composition is encapsulated or compressed into a tablet.

20. The pharmaceutical composition according to claim 3, wherein the potassium salt of Compound A is employed in an amount of 50 wt. % and the hydroxyproylmethylcellulose is employed in an amount in a range of from 2 wt. % to 15 wt. %.

21. The pharmaceutical composition according to claim 20, wherein the hydroxyproylmethylcellulose is employed in an amount of 5 wt. %.

22. The pharmaceutical composition according to claim 3, wherein the hydroxyproylmethylcellulose is a low-viscosity hydroxypropylmethylcellulose.

23. The pharmaceutical composition according to claim 22, wherein the potassium salt of Compound A is employed in an amount of 50 wt. % and the low-viscosity hydroxyproylmethylcellulose is employed in an amount in a range of from 2 wt. % to 15 wt. %.

24. The pharmaceutical composition according to claim 23, wherein the low-viscosity hydroxyproylmethylcellulose is employed in an amount of 5 wt. %.

25. The pharmaceutical composition according to claim 1, wherein the potassium salt of Compound A exhibits improved pharmacokinetic properties when administered as a component of this composition.

* * * * *